US008281557B2

(12) United States Patent
Doshi et al.

(10) Patent No.: US 8,281,557 B2
(45) Date of Patent: Oct. 9, 2012

(54) METHOD OF PACKAGING AND DISPENSING NASAL DEVICES

(75) Inventors: Rajiv Doshi, Los Altos, CA (US); Bryan Loomas, Los Gatos, CA (US); Enrique F. Mendez, Danville, CA (US); Arthur G. Sandoval, San Francisco, CA (US); Jeffrey W. Servaites, San Francisco, CA (US); Matthew Durack, San Francisco, CA (US)

(73) Assignee: Ventus Medical, Inc., San Jose, CA (US)

( * ) Notice: Subject to any disclaimer, the term of this patent is extended or adjusted under 35 U.S.C. 154(b) by 0 days.

(21) Appl. No.: 13/212,948

(22) Filed: Aug. 18, 2011

(65) Prior Publication Data

US 2012/0031048 A1 Feb. 9, 2012

Related U.S. Application Data

(63) Continuation of application No. 12/329,271, filed on Dec. 5, 2008, now Pat. No. 8,020,700.

(60) Provisional application No. 60/992,655, filed on Dec. 5, 2007.

(51) Int. Cl.

| | |
|---|---|
| *B65B 55/04* | (2006.01) |
| *B65B 15/00* | (2006.01) |
| *B65B 25/00* | (2006.01) |
| *A61F 5/56* | (2006.01) |
| *A62B 23/06* | (2006.01) |

(52) U.S. Cl. ........ 53/426; 53/467; 128/207.18; 128/848

(58) Field of Classification Search .................... 53/426, 53/443, 446, 447, 467; *B65B 15/00, 15/02, B65B 23/00, 25/00*

See application file for complete search history.

(56) References Cited

U.S. PATENT DOCUMENTS 69,396 A 10/1867 Curtis
628,111 A 7/1899 McHatton (Continued)

FOREIGN PATENT DOCUMENTS

EP 0 434 258 A2 6/1991

(Continued)

OTHER PUBLICATIONS

Sather et al.; U.S. Appl. No. 13/117,933 entitled "Layered nasal respiratory devices," filed May 27, 2011.

(Continued)

*Primary Examiner* — Stephen F Gerrity
(74) *Attorney, Agent, or Firm* — Shay Glenn LLP

(57) ABSTRACT

Described herein are packaging systems for nasal devices, and methods of packaging and/or dispensing nasal devices. A packaging system may include one or a plurality of nasal devices removably secured to a support backing, and a dispenser. In some variations an applicator may also be included. Methods of using and methods of assembling packaging systems and dispensers are also described.

19 Claims, 31 Drawing Sheets

U.S. PATENT DOCUMENTS

| | | | | | |
|---|---|---|---|---|---|
| 669,098 | A | | 3/1901 | Overshiner | |
| 675,275 | A | | 5/1901 | Gunning | |
| 718,785 | A | | 1/1903 | McNary | |
| 746,869 | A | | 12/1903 | Moulton | |
| 774,446 | A | | 11/1904 | Moulton | |
| 810,617 | A | | 1/1906 | Carence | |
| 1,819,884 | A | | 8/1931 | Fores | |
| 2,198,959 | A | | 4/1940 | Clarke | |
| 2,237,954 | A | | 4/1941 | Wilson | |
| 2,264,153 | A | | 11/1941 | Rowe | |
| 2,274,886 | A | | 3/1942 | Carroll | |
| 2,282,681 | A | | 5/1942 | Stotz | |
| 2,335,936 | A | | 12/1943 | Hanlon | |
| 2,433,565 | A | | 12/1947 | Korman | |
| 2,448,724 | A | | 9/1948 | McGovney | |
| 2,593,315 | A | | 4/1952 | Kraft | |
| 2,672,138 | A | | 3/1954 | Carlock | |
| 2,751,906 | A | | 6/1956 | Irvine | |
| 2,777,442 | A | | 1/1957 | Zelano | |
| 3,145,711 | A | | 8/1964 | Beber | |
| 3,370,305 | A | | 2/1968 | Goott et al. | |
| 3,451,392 | A | | 6/1969 | Cook et al. | |
| 3,463,149 | A | | 8/1969 | Albu | |
| 3,513,839 | A | | 5/1970 | Vacante | |
| 3,556,122 | A | | 1/1971 | Laerdal | |
| 3,616,802 | A | | 11/1971 | Marinaccio | |
| 3,657,855 | A | * | 4/1972 | Swezey | 53/397 |
| 3,695,265 | A | | 10/1972 | Brevik | |
| 3,710,799 | A | | 1/1973 | Caballero | |
| 3,722,509 | A | | 3/1973 | Nebel | |
| 3,747,597 | A | | 7/1973 | Olivera | |
| 3,802,426 | A | * | 4/1974 | Sakamoto | 128/206.11 |
| 3,884,223 | A | | 5/1975 | Keindl | |
| 3,902,621 | A | | 9/1975 | Hidding | |
| 4,004,584 | A | | 1/1977 | Geaney | |
| 4,030,491 | A | | 6/1977 | Mattila | |
| 4,040,428 | A | | 8/1977 | Clifford | |
| 4,054,134 | A | | 10/1977 | Kritzer | |
| 4,062,358 | A | | 12/1977 | Kritzer | |
| 4,094,316 | A | | 6/1978 | Nathanson | |
| 4,143,872 | A | | 3/1979 | Havstad et al. | |
| 4,212,296 | A | | 7/1980 | Schaar | |
| 4,220,150 | A | | 9/1980 | King | |
| 4,221,217 | A | | 9/1980 | Amezcua | |
| 4,226,233 | A | | 10/1980 | Kritzer | |
| 4,240,420 | A | | 12/1980 | Riaboy | |
| 4,267,831 | A | | 5/1981 | Aguilar | |
| 4,327,719 | A | | 5/1982 | Childers | |
| RE31,040 | E | | 9/1982 | Possis | |
| 4,354,489 | A | | 10/1982 | Riaboy | |
| 4,403,616 | A | | 9/1983 | King | |
| 4,456,016 | A | | 6/1984 | Nowacki et al. | |
| 4,487,207 | A | | 12/1984 | Fitz | |
| 4,533,137 | A | | 8/1985 | Sonne | |
| 4,582,058 | A | | 4/1986 | Depel et al. | |
| 4,601,465 | A | | 7/1986 | Roy | |
| 4,640,277 | A | | 2/1987 | Meyer et al. | |
| 4,651,873 | A | | 3/1987 | Stolcenberg et al. | |
| 4,702,374 | A | * | 10/1987 | Kelner | 206/418 |
| 4,718,554 | A | * | 1/1988 | Barbato | 206/477 |
| 4,739,987 | A | | 4/1988 | Nicholson | |
| 4,822,354 | A | | 4/1989 | Elosegui | |
| 4,854,574 | A | | 8/1989 | Larson et al. | |
| 4,860,766 | A | | 8/1989 | Sackner | |
| 4,862,903 | A | | 9/1989 | Campbell | |
| 4,908,028 | A | | 3/1990 | Colon et al. | |
| 4,913,138 | A | | 4/1990 | Yoshida et al. | |
| 4,919,138 | A | | 4/1990 | Nordenstroom | |
| 4,973,047 | A | | 11/1990 | Norell | |
| 4,979,505 | A | | 12/1990 | Cox | |
| 4,984,302 | A | | 1/1991 | Lincoln | |
| 4,984,581 | A | | 1/1991 | Stice | |
| 5,016,425 | A | * | 5/1991 | Weick | 53/453 |
| 5,033,312 | A | | 7/1991 | Stupecky | |
| 5,038,621 | A | | 8/1991 | Stupecky | |
| 5,059,208 | A | | 10/1991 | Coe et al. | |
| 5,074,293 | A | | 12/1991 | Lott et al. | |
| 5,078,739 | A | | 1/1992 | Martin | |
| 5,092,781 | A | | 3/1992 | Casciotti et al. | |
| 5,117,820 | A | | 6/1992 | Robitaille | |
| 5,197,980 | A | | 3/1993 | Gorshkov et al. | |
| 5,255,687 | A | | 10/1993 | McKenna | |
| 5,383,470 | A | | 1/1995 | Kolbly | |
| 5,385,542 | A | | 1/1995 | Rawlings | |
| 5,391,205 | A | | 2/1995 | Knight | |
| 5,392,773 | A | | 2/1995 | Bertrand | |
| 5,394,867 | A | | 3/1995 | Swann | |
| 5,414,627 | A | | 5/1995 | Wada et al. | |
| 5,415,660 | A | | 5/1995 | Campbell et al. | |
| 5,425,359 | A | | 6/1995 | Liou | |
| 5,459,544 | A | | 10/1995 | Emura | |
| 5,522,382 | A | | 6/1996 | Sullivan et al. | |
| 5,535,739 | A | | 7/1996 | Rapoport et al. | |
| 5,562,641 | A | | 10/1996 | Flomenblit et al. | |
| 5,568,808 | A | | 10/1996 | Rimkus | |
| 5,607,469 | A | | 3/1997 | Frey | |
| 5,649,533 | A | | 7/1997 | Oren | |
| 5,665,104 | A | | 9/1997 | Lee | |
| 5,727,546 | A | | 3/1998 | Clarke et al. | |
| 5,740,798 | A | | 4/1998 | McKinney | |
| 5,743,256 | A | | 4/1998 | Jalowayski | |
| 5,763,979 | A | | 6/1998 | Mukherjee et al. | |
| 5,775,335 | A | | 7/1998 | Seal | |
| 5,782,896 | A | | 7/1998 | Chen et al. | |
| 5,797,920 | A | | 8/1998 | Kim | |
| 5,803,121 | A | | 9/1998 | Estes | |
| 5,823,187 | A | | 10/1998 | Estes et al. | |
| 5,865,170 | A | | 2/1999 | Moles | |
| 5,876,434 | A | | 3/1999 | Flomenblit et al. | |
| 5,890,998 | A | | 4/1999 | Hougen | |
| 5,899,832 | A | | 5/1999 | Hougen | |
| 5,910,071 | A | | 6/1999 | Hougen | |
| 5,911,756 | A | | 6/1999 | Debry | |
| 5,947,119 | A | | 9/1999 | Reznick | |
| 5,954,766 | A | | 9/1999 | Zadno-Azizi et al. | |
| 5,957,978 | A | | 9/1999 | Blom | |
| 5,992,006 | A | | 11/1999 | Datsikas | |
| 6,004,342 | A | | 12/1999 | Filis | |
| 6,058,932 | A | | 5/2000 | Hughes | |
| 6,083,141 | A | | 7/2000 | Hougen | |
| D430,667 | S | | 9/2000 | Rome | |
| 6,119,690 | A | | 9/2000 | Pantaleo | |
| 6,165,133 | A | | 12/2000 | Rapoport et al. | |
| 6,177,482 | B1 | | 1/2001 | Cinelli et al. | |
| 6,189,532 | B1 | | 2/2001 | Hely et al. | |
| 6,213,955 | B1 | | 4/2001 | Karakasoglu et al. | |
| 6,219,997 | B1 | * | 4/2001 | Friberg et al. | 53/467 |
| 6,258,100 | B1 | | 7/2001 | Alferness et al. | |
| 6,287,290 | B1 | | 9/2001 | Perkins et al. | |
| 6,293,951 | B1 | | 9/2001 | Alferness et al. | |
| 6,311,839 | B1 | * | 11/2001 | Lo | 206/371 |
| 6,369,126 | B1 | | 4/2002 | Cinelli et al. | |
| 6,398,775 | B1 | | 6/2002 | Perkins et al. | |
| 6,439,233 | B1 | | 8/2002 | Geertsema | |
| 6,484,725 | B1 | | 11/2002 | Chi | |
| 6,500,095 | B1 | | 12/2002 | Hougen | |
| 6,510,846 | B1 | | 1/2003 | O'Rourke | |
| 6,527,761 | B1 | | 3/2003 | Soltesz et al. | |
| 6,561,188 | B1 | | 5/2003 | Ellis | |
| 6,562,057 | B2 | | 5/2003 | Santin | |
| 6,568,387 | B2 | | 5/2003 | Davenport et al. | |
| 6,573,421 | B1 | | 6/2003 | Lemaire | |
| 6,581,598 | B1 | | 6/2003 | Foran et al. | |
| 6,585,639 | B1 | | 7/2003 | Kotmel et al. | |
| 6,592,594 | B2 | | 7/2003 | Rimbaugh et al. | |
| 6,592,995 | B2 | | 7/2003 | Topolkaraev et al. | |
| 6,595,215 | B2 | | 7/2003 | Wood | |
| 6,609,516 | B2 | | 8/2003 | Hollander et al. | |
| 6,626,172 | B1 | | 9/2003 | Karow et al. | |
| 6,626,179 | B1 | | 9/2003 | Pedley | |
| 6,631,721 | B1 | | 10/2003 | Salter et al. | |
| 6,679,264 | B1 | | 1/2004 | Deem et al. | |
| 6,694,979 | B2 | | 2/2004 | Deem et al. | |
| 6,722,360 | B2 | | 4/2004 | Doshi | |
| 6,726,598 | B1 | | 4/2004 | Jarvis et al. | |
| 6,737,160 | B1 | | 5/2004 | Full et al. | |
| 6,769,432 | B1 | | 8/2004 | Keifer | |

| | | | | |
|---|---|---|---|---|
| 6,776,162 | B2 | 8/2004 | Wood | |
| 6,811,538 | B2 | 11/2004 | Westbrook et al. | |
| 6,841,716 | B1 | 1/2005 | Tsutsumi | |
| 6,848,446 | B2 | 2/2005 | Noble | |
| 6,863,066 | B2 | 3/2005 | Ogle | |
| 6,866,652 | B2 | 3/2005 | Bierman | |
| 6,872,439 | B2 | 3/2005 | Fearing et al. | |
| 6,921,574 | B2 | 7/2005 | Cinelli et al. | |
| 6,997,177 | B2 | 2/2006 | Wood | |
| 7,011,723 | B2 | 3/2006 | Full et al. | |
| 7,047,969 | B2 | 5/2006 | Noble | |
| 7,156,098 | B2 | 1/2007 | Dolezal et al. | |
| 7,175,723 | B2 | 2/2007 | Jones et al. | |
| 7,178,524 | B2 | 2/2007 | Noble | |
| 7,201,169 | B2 | 4/2007 | Wilkie et al. | |
| D542,407 | S | 5/2007 | Stallard et al. | |
| 7,263,996 | B2 | 9/2007 | Yung Ho | |
| 7,334,581 | B2 | 2/2008 | Doshi | |
| D566,834 | S | 4/2008 | Barton | |
| 7,422,014 | B1 | 9/2008 | Smith | |
| 7,506,649 | B2 | 3/2009 | Doshi et al. | |
| 7,559,326 | B2 | 7/2009 | Smith et al. | |
| 7,640,934 | B2 | 1/2010 | Zollinger et al. | |
| 7,735,491 | B2 | 6/2010 | Doshi et al. | |
| 7,735,492 | B2 | 6/2010 | Doshi et al. | |
| 7,798,148 | B2 | 9/2010 | Doshi et al. | |
| 7,806,120 | B2 | 10/2010 | Loomas et al. | |
| 7,856,979 | B2 | 12/2010 | Doshi et al. | |
| 7,880,051 | B2 | 2/2011 | Madsen et al. | |
| 7,987,852 | B2 | 8/2011 | Doshi et al. | |
| 7,992,563 | B2 | 8/2011 | Doshi | |
| 7,992,564 | B2 | 8/2011 | Doshi et al. | |
| 8,020,700 | B2 | 9/2011 | Doshi et al. | |
| 8,061,357 | B2 | 11/2011 | Pierce et al. | |
| 2001/0051799 | A1 | 12/2001 | Ingenito | |
| 2001/0056274 | A1 | 12/2001 | Perkins et al. | |
| 2002/0062120 | A1 | 5/2002 | Perkins et al. | |
| 2002/0077593 | A1 | 6/2002 | Perkins et al. | |
| 2002/0112729 | A1 | 8/2002 | DeVore et al. | |
| 2002/0157673 | A1 | 10/2002 | Kessler et al. | |
| 2003/0024527 | A1 | 2/2003 | Ginn | |
| 2003/0050648 | A1 | 3/2003 | Alferness et al. | |
| 2003/0070682 | A1 | 4/2003 | Wilson et al. | |
| 2003/0106555 | A1 | 6/2003 | Tovey | |
| 2003/0106556 | A1 | 6/2003 | Alperovich et al. | |
| 2003/0140925 | A1 | 7/2003 | Sapienza et al. | |
| 2003/0149387 | A1* | 8/2003 | Barakat et al. | 602/45 |
| 2003/0154988 | A1 | 8/2003 | DeVore et al. | |
| 2003/0158515 | A1 | 8/2003 | Gonzalez et al. | |
| 2003/0195552 | A1 | 10/2003 | Santin | |
| 2003/0209247 | A1 | 11/2003 | O'Rourke | |
| 2004/0016432 | A1 | 1/2004 | Genger et al. | |
| 2004/0020492 | A1 | 2/2004 | Dubrul et al. | |
| 2004/0020493 | A1 | 2/2004 | Wood | |
| 2004/0055606 | A1 | 3/2004 | Hendricksen et al. | |
| 2004/0112379 | A1 | 6/2004 | Djupesland | |
| 2004/0123868 | A1 | 7/2004 | Rutter | |
| 2004/0149615 | A1* | 8/2004 | Eisenbraun | 53/467 |
| 2004/0254491 | A1 | 12/2004 | Ricciardelli | |
| 2004/0261791 | A1 | 12/2004 | Horian | |
| 2004/0261798 | A1 | 12/2004 | Rimkus | |
| 2005/0010125 | A1 | 1/2005 | Joy et al. | |
| 2005/0011524 | A1 | 1/2005 | Thomlinson et al. | |
| 2005/0033344 | A1 | 2/2005 | Dillard et al. | |
| 2005/0051170 | A1 | 3/2005 | Koo | |
| 2005/0066965 | A1 | 3/2005 | Cronk et al. | |
| 2005/0133039 | A1 | 6/2005 | Wood | |
| 2005/0279351 | A1 | 12/2005 | Lewis et al. | |
| 2005/0284479 | A1 | 12/2005 | Schrader et al. | |
| 2006/0000472 | A1 | 1/2006 | Fenton | |
| 2006/0016450 | A1 | 1/2006 | Pearson et al. | |
| 2006/0085027 | A1 | 4/2006 | Santin et al. | |
| 2006/0169285 | A1 | 8/2006 | Bovo | |
| 2006/0180149 | A1 | 8/2006 | Matarasso | |
| 2006/0266361 | A1 | 11/2006 | Hernandez | |
| 2006/0283461 | A1 | 12/2006 | Lubke et al. | |
| 2007/0016123 | A1 | 1/2007 | Jensen | |
| 2007/0051364 | A1 | 3/2007 | Jacobson et al. | |
| 2007/0095349 | A1 | 5/2007 | Hansmann et al. | |
| 2007/0175478 | A1 | 8/2007 | Brunst | |
| 2007/0227542 | A1 | 10/2007 | Kashmakov et al. | |
| 2007/0283962 | A1 | 12/2007 | Doshi et al. | |
| 2007/0287976 | A1 | 12/2007 | Sherrill | |
| 2008/0023007 | A1 | 1/2008 | Dolezal et al. | |
| 2008/0032119 | A1 | 2/2008 | Feldhahn et al. | |
| 2008/0041397 | A1 | 2/2008 | Hirs | |
| 2008/0053460 | A1 | 3/2008 | Wilson | |
| 2008/0087286 | A1 | 4/2008 | Jones | |
| 2008/0099021 | A1 | 5/2008 | Moore | |
| 2008/0142014 | A1 | 6/2008 | Jiang | |
| 2008/0142018 | A1 | 6/2008 | Doshi et al. | |
| 2008/0178874 | A1 | 7/2008 | Doshi et al. | |
| 2008/0221470 | A1 | 9/2008 | Sather et al. | |
| 2009/0145441 | A1 | 6/2009 | Doshi et al. | |
| 2009/0194100 | A1 | 8/2009 | Minagi | |
| 2009/0194109 | A1 | 8/2009 | Doshi et al. | |
| 2009/0241965 | A1 | 10/2009 | Sather et al. | |
| 2009/0308398 | A1 | 12/2009 | Ferdinand et al. | |
| 2010/0326447 | A1 | 12/2010 | Loomas et al. | |
| 2011/0005520 | A1 | 1/2011 | Doshi et al. | |
| 2011/0005528 | A1 | 1/2011 | Doshi et al. | |
| 2011/0005529 | A1 | 1/2011 | Doshi et al. | |
| 2011/0005530 | A1 | 1/2011 | Doshi et al. | |
| 2011/0056499 | A1 | 3/2011 | Doshi et al. | |
| 2011/0067708 | A1 | 3/2011 | Doshi et al. | |
| 2011/0067709 | A1 | 3/2011 | Doshi et al. | |
| 2011/0108041 | A1 | 5/2011 | Sather et al. | |
| 2011/0203598 | A1 | 8/2011 | Favet et al. | |
| 2011/0218451 | A1 | 9/2011 | Lai et al. | |
| 2011/0240032 | A1 | 10/2011 | Doshi | |
| 2011/0240038 | A1 | 10/2011 | Doshi et al. | |
| 2012/0055488 | A1 | 3/2012 | Pierce et al. | |

FOREIGN PATENT DOCUMENTS

| | | | | |
|---|---|---|---|---|
| EP | 1157663 | A1 | | 11/2001 |
| EP | 1205203 | A2 | | 5/2002 |
| EP | 1481702 | A2 | | 12/2004 |
| FR | 2862614 | A1 | * | 5/2005 |
| GB | 2096574 | A | * | 10/1982 |
| GB | 2324729 | A | | 4/1998 |
| JP | 52123786 | A | * | 10/1977 |
| JP | 55-122742 | U | | 9/1980 |
| JP | 58-136345 | A | | 8/1983 |
| JP | 63-189257 | U | | 12/1988 |
| JP | 7-47126 | | | 2/1995 |
| JP | 3059270 | U | | 3/1999 |
| JP | 2001-299916 | A | | 10/2001 |
| JP | 2002153489 | A | * | 5/2002 |
| JP | 2002-219174 | A | | 8/2002 |
| JP | 2002-345963 | A | | 12/2002 |
| JP | 2002-345966 | | | 12/2002 |
| JP | 05/40589 | A | | 2/2005 |
| JP | 2005-505355 | | | 2/2005 |
| JP | 2008-136496 | | | 6/2008 |
| JP | 2008-522763 | | | 7/2008 |
| RU | 2048820 | C1 | | 11/1995 |
| SU | 1586709 | A1 | | 8/1990 |
| WO | WO 90/12614 | A1 | | 11/1990 |
| WO | WO 93/08777 | A1 | | 5/1993 |
| WO | WO 95/17220 | A1 | | 6/1995 |
| WO | WO 95/33520 | A1 | | 12/1995 |
| WO | WO 99/03395 | A1 | | 1/1999 |
| WO | WO 00/29066 | A1 | | 5/2000 |
| WO | WO 00/50121 | A1 | | 8/2000 |
| WO | WO 00/67848 | A1 | | 11/2000 |
| WO | WO 01/02042 | A1 | | 1/2001 |
| WO | WO 01/13839 | A1 | | 3/2001 |
| WO | WO 01/13908 | A2 | | 3/2001 |
| WO | WO 01/49371 | A2 | | 7/2001 |
| WO | WO 01/87170 | A1 | | 11/2001 |
| WO | WO 01/89381 | A1 | | 11/2001 |
| WO | WO 02/38038 | A2 | | 5/2002 |
| WO | WO 03/022124 | A2 | | 3/2003 |
| WO | WO 03/034927 | A1 | | 5/2003 |
| WO | WO 2004/084998 | A1 | | 10/2004 |
| WO | WO2005/000805 | A2 | | 1/2005 |
| WO | WO2006/040585 | A1 | | 4/2006 |
| WO | WO2007/023607 | | | 3/2007 |

| | | | |
|---|---|---|---|
| WO | WO 2007/129814 | A1 | 11/2007 |
| WO | WO 2007/134458 | A1 | 11/2007 |
| WO | WO 2007/146133 | A2 | 12/2007 |

OTHER PUBLICATIONS http://chinookmed.com/index.cfm/fa/product.display&Product_ID=275; accessed Nov. 28, 2007.

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

Dillard, D. et al., Evaluation of a novel intra-bronchial valve to produce lung volume reduction, World Congress of Bronchology, Jun. 2002 (figs. 1-4 available upon request).

Hakel et al.; Nasal obturator for velopharyngeal dysfunction in dysarthria: technical report on a one-way valve; Journal of Medical Speech-Language Pathology; vol. 12; No. 4; pp. 155-159; 2004.

Suwaki et al.; Nasal speaking valve: a device for managing velopharyngeal incompetence; Journal of Oral Rehabilitation; vol. 35; pp. 73-78; 2008.

Suwaki et al.; The effect of nasal speaking valve on the speech under experimental velopharyngeal incompetence condition; Journal of Oral Rehabilitation; vol. 35; pp. 361-369; 2008.

* cited by examiner

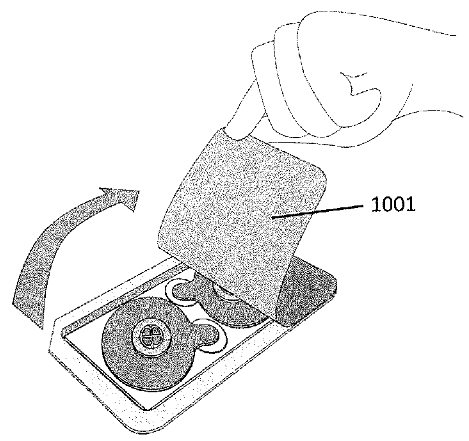
FIG. 10A
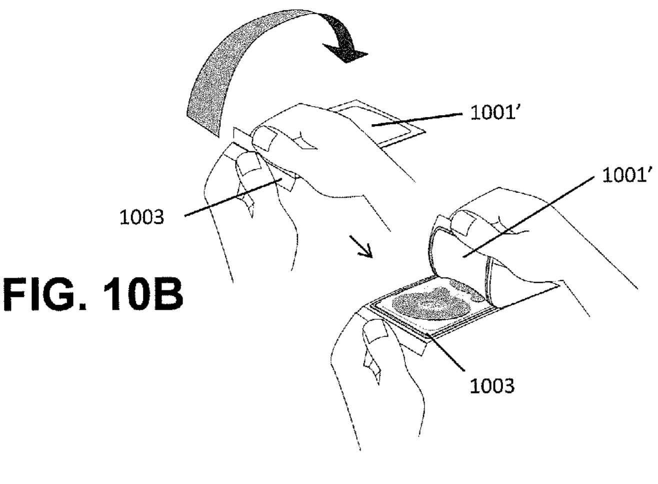
FIG. 10B
FIG. 10C

METHOD OF PACKAGING AND DISPENSING NASAL DEVICES

CROSS-REFERENCE TO RELATED APPLICATION

This application is a continuation of U.S. patent application Ser. No. 12/329,271, filed Dec. 5, 2008, now U.S. Pat. No. 8,020,700, titled "Packaging and Dispensing Nasal Devices, which claims priority to U.S. Provisional Patent Application No. 60/992,655, filed Dec. 5, 2007, titled "Packaging and Dispensing Nasal Devices".

BACKGROUND

Nasal respiratory devices have been well-described in the following U.S. patent applications, each of which is incorporated herein in its entirety: U.S. patent application Ser. No. 11/298,640 (titled "NASAL RESPIRATORY DEVICES") filed Dec. 8, 2005; U.S. patent application Ser. No. 11/298,339 (titled "RESPIRATORY DEVICES") filed Dec. 8, 2005; and U.S. patent application Ser. No. 11/298,362 (titled "METHODS OF TREATING RESPIRATORY DISORDERS") filed Dec. 8, 2005; U.S. patent application Ser. No. 11/805,496 (titled "NASAL RESPIRATORY DEVICES") filed May 22, 2007; U.S. patent application Ser. No. 11/759,916 (titled "LAYERED NASAL DEVICES") filed Jun. 7, 2007; U.S. patent application Ser. No. 11/811,339 (titled "NASAL DEVICES") filed Jun. 7, 2007; and U.S. patent application Ser. No. 11/811,401 (titled "NASAL RESPIRATORY DEVICES FOR POSITIVE END-EXPIRATORY PRESSURE") filed Jun. 7, 2007. Each of these patent applications is incorporated herein by reference in its entirety.

These patent applications generally describe nasal respiratory devices and methods for treating a variety of medical conditions through the use of such devices. These medical conditions include but are not limited to snoring, sleep apnea (obstructive, central, complex and mixed), Cheyne Stokes breathing, UARS, COPD, hypertension, asthma, GERD, heart failure, and other respiratory and sleep conditions. Such nasal respiratory devices are typically adapted to be removably secured in communication with a nasal cavity. The nasal respiratory devices described herein may include any devices having one or more airflow resistor valves. These devices may include a passageway with an opening at a proximal end and an opening at a distal end, a valve (or airflow resistor) in communication with the passageway, and a holdfast in communication with the outer walls forming the passageway. The holdfast may be configured to removably secure the respiratory device within (or over or around) the nasal cavity. Adhesive holdfasts are of particular interest, and may be referred to as adhesive nasal devices or adhesive nasal respiratory devices.

Many of the nasal devices previously described are adhesive nasal respiratory devices including layered nasal respiratory devices. In some instances, the devices are configured so that each device communicates with a single nostril, and thus a pair of devices may be used at a time. In some variations the devices may be configured so that a single device communicates with both nostrils. Furthermore, the devices may be disposable, so that a subject can use a new pair of devices (comprising one "dose") and then throw them out. A nasal device may also include an odorant, a medicament, and/or some other active agent. For all of these reasons, it may be important to effectively package and dispense these nasal devices. These nasal devices include an airflow resistor that must meet preset quality and functional parameters. Thus, it would be highly beneficial for the packaging to accommodate testing and protection of elements such as the airflow resistor. Thus, there is a need for accurate, efficient, and cost-effective ways to package and dispense nasal respiratory devices. Described herein are systems, devices, and methods that may address some of these needs.

SUMMARY

Described herein are packaging systems for nasal devices, dispensers for nasal devices, and methods of packaging and/or dispensing nasal devices. The nasal devices referred to wherein typically include one or more airflow resistors configured to inhibit exhalation more than inhalation. These nasal devices are generally passive resistance devices (e.g., devices that do not require the addition of pressurized air to increase the resistance to exhalation), and are typically low-profile, compact devices that may be comfortably worn by a sleeping subject. These nasal devices may be configured to communicate with both of a subject's nostrils (e.g., a whole-nose device) or they may be configured to communicate with only a single nostril.

A packaging system for dispensing adhesive nasal devices may generally include one or a plurality of nasal devices (e.g., adhesive nasal devices that are configured to be adhesively secured to a subject's nose), wherein each nasal device includes an airflow resistor that inhibits exhalation more than inhalation, and a support backing to which at least one of the nasal devices is removably secured. A packaging system may also include a dispenser having a dispenser housing that at least partially surrounds the removably linked adhesive nasal devices.

The support backing may be an adhesive substrate to which the adhesive nasal device is removably affixed. For example, a support backing may include a substantially non-stick surface. The support backing may be a smooth and/or waxy surface to which the adhesive substrate of the adhesive holdfast can be removably attached. An adhesive nasal device can be removed from the support backing by applying force (e.g., by peeling the adhesive nasal device from the support backing) or by applying an agent (e.g., a solvent, including water) to release the adhesive holdfast and/or activate the adhesive. Removing the adhesive nasal device from the support backing may expose all or a portion of the adhesive holdfast of the nasal device so that it can be secured to a subject. The support backing may be a thin material such as a paper or cloth and may be made of any appropriate material, including polymeric materials, metallic foils, or the like. The surface of the support backing to which the adhesive nasal device attaches may be treated so that the nasal device may be readily released (e.g., by peeling). As mentioned, the support backing may include a surface that allows the adhesive holdfast of the nasal device to be removed so that the adhesive can then be applied to the skin. In some variations, the support backing has a substantially non-stick surface (e.g., a silicone coating, a wax coating, etc.). In some variations, the support backing includes a surface that is made of a polymeric material (e.g., plastic). The surface may be a layer of the support backing.

In some variations the nasal device is formed on the support backing. For example, the support backing may be one or more of the layers forming the adhesive nasal device, such as the adhesive substrate layer. Thus, the support layer may be perforated or pre-cut (at least partially cut) to allow removal of the adhesive nasal devices.

In some variations, the packaging system including a support backing may be configured as a card, a roll or a stack. For example, one or a pair of adhesive nasal devices may be attached to a support backing configured as a card. Two or more adhesive nasal devices may be removably attached to an elongated support backing that may be rolled so that individual adhesive nasal devices may be dispensed by removing them from the roll. A stack of adhesive nasal devices may be formed by folding the support backing to which the adhesive nasal devices are attached. Alternatively, a stack of adhesive nasal devices may be formed by attaching a first nasal device to the support backing, and then sequentially attaching additional nasal devices onto this first nasal device. Thus, each nasal device may support an adjacent nasal device, and nasal devices may be removed from each other until the first nasal device (and the support backing) is exposed.

The support backing may include an adhesive substrate. The support backing may be flat or planar. As used herein flat or planar substrates may be stiff or flexible (e.g., bendable). For example, in one variation the support backing may be a card. The support backing may be any appropriate size. For example, the support backing may be sized to fit into a pocket, wallet, or carrying case. A support backing may be shaped as a rectangle, square, oval, or other shape. In some variations, the support backing is less than 5 inches in diameter.

As mentioned, any appropriate nasal device(s) may be removably secured to the support backing. In particular, adhesive nasal devices having an adhesive holdfast and an airflow resistor may be used. Examples of nasal devices that may be used are described below, and in the patent applications mentioned and incorporated by reference above, including U.S. patent application Ser. No. 11/759,916 (titled "LAYERED NASAL DEVICES") filed Jun. 7, 2007; U.S. patent application Ser. No. 11,811,339 (titled "NASAL DEVICES") filed Jun. 7, 2007; and U.S. patent application Ser. No. 11/811,401 (titled "NASAL RESPIRATORY DEVICES FOR POSITIVE END-EXPIRATORY PRESSURE") filed Jun. 7, 2007.

The packaging system may also include one or more features to assist in removing the nasal device(s) from the support backing. For example, the support backing may include a bend axis, wherein the bend axis is configured so that the backing may be preferentially bent along the bend axis. Bending the axis of the support backing may expose a region of the removable nasal device so that it can be grasped. The bend axis may be a crease in the support backing, a hinged region of the support axes, a pre-bent region, a scored region, a region in which material has been removed along the axis (a cut region), etc.

In general, the support backing may include an opening to which the airflow resistor (or airflow resistors) of one or more nasal devices may be aligned. This opening (or thru-hole) through the support backing typically allows air to be passed through the airflow resistor of the nasal device when it is secured to the support backing without requiring the nasal device to be removed from the support backing. This may be particularly useful for testing the resistance of the nasal device (e.g., the airflow resistor). In some variations the airflow resistor passes at least partially through the opening in the support backing. In some variations the opening is a cut out region that is removed from the support backing; in other variations the opening is not formed by a removed region, but is instead formed by a flap or cut in the support backing that maybe moved out of the way to form the opening.

A packaging system may also include at least one opening through the support backing that is useful for removing the one or more nasal devices. Such openings may be referred to as finger or detachment openings, because they may aid in detaching the nasal device from the support backing by allowing a subject to manually grasp the nasal device and separate it from the support backing. In some variations, the support backing including detachment openings associated with each nasal device. A portion of the nasal device (e.g., a tab or handle region) may extend into or across the detachment opening through the support backing, and allow the device to be more readily removed from the support backing.

Similarly, a packaging system may also include a cut region (e.g., a partially cut out opening) through the support backing to assist with removal of the device. The cut region is typically associated with each nasal device. For example, the support backing may be perforated. In some variations, the cut region is a semicircular cut through the support backing around a tab or handle of a nasal device that is removably attached to the support backing. The cut region may form the bend axis, as described above. Cut regions that are used for helping remove the nasal device from the support backing may be referred to as detachment cuts or detachment cut regions.

A packaging system for dispensing adhesive nasal devices may also include a dispenser housing (or "housing") that at least partially surrounds the plurality of adhesive nasal devices. A dispenser housing is typically configured to hold the support backing and nasal devices. The dispenser may be single-use or multi-use. A single-use dispenser may be configured as a pouch or tray configured to hold a pair of adhesive nasal devices. In some variations, the dispenser may be configured to hold a single nasal device. For example, a single-use dispenser may be a plastic, paper or foil pouch surrounding one or a pair of nasal devices (e.g., a first nasal device and a second nasal device). In some variations, the first and second nasal devices are configured to attach to different nostrils. For example, in some variations, the first nasal device is configured to be placed in communication with a subject's left nostril, and the second nasal device is configured to be placed in communication with the subject's right nostril. In some variations, the nasal devices are identical, and can be placed in communication with either of the subject's nostrils. In some variations, the nasal device is a whole-nose nasal device.

The dispenser housing may be sealed, and can be sterilized or sterilizable. For example, the system may include a dispenser housing into which a support backing and one or more nasal devices releasably secured to the support backing are placed. The dispenser housing may be made of any appropriate material, including paper, plastic, metal (e.g., foil), or the like. For example, the dispenser may be a pouch formed of waxed paper. In some variations, the support backing forms one portion of the sealable dispenser. For example, the support backing may be folded back onto itself to enclose the attached nasal devices.

In some variation, the dispenser may include a cover, lid or other entry structure that may be opened to dispense the nasal device(s). For example, a dispenser may be configured as a pouch that includes a tear line indicating a location long which the pouch may be opened. If Single-use dispensers may be made of a material that can be torn (e.g., paper, foil, etc.).

As mentioned, the dispenser may comprise a tray to hold nasal devices. The tray may be made of any appropriate material, and may have a bottom and sides. The tray may be covered with a cover. The cover may be sealed over the tray, securing a support backing and attached nasal devices inside the tray. In some variations, the cover is removable to expose the nasal devices on the support backing. In some variations, the bottom of the tray is the support backing.

A dispenser may be a multi-use dispenser that may include a durable housing from which individual (or pairs) of nasal device can be sequentially removed. The multi-use dispenser may include a closable lid or opening from which nasal devices can be withdrawn. In some variations, the dispenser housing is made of a polymeric material (e.g., plastic), and can include a handle. A dispenser housing may also be mountable (e.g., to a bed, table, etc.). A multi-use dispenser may have a control (e.g., button, slider, etc.) for dispensing one or more nasal devices from the housing. In some variations, the dispenser also includes an indicator to inform a user that the dispenser is empty, nearly empty, or the number of nasal devices remaining. For example, the dispenser may include a window showing the remaining nasal devices. The multi-use dispenser may be refillable with additional adhesive nasal devices.

In some variations, the dispenser is configured as a tray to hold the support backing and nasal devices. For example, the support backing may be affixed (or part of) the bottom the tray. The tray may be opened by peeling off a cover, allowing access to the nasal devices therein.

A packaging system for dispensing nasal devices may also include a case that is configured to hold a plurality of dispenser housings. For example, a case may be a box having a plurality of dispensers therein. In some variations, the case may include a recommended course of treatment using the nasal devices. For example, a case may include a months worth of single-use dispensers, each containing a pair of nasal devices or a single whole-nose device (e.g., 30 or so single-use dispensers). A case may be formed of a relatively stiff material (e.g., plastic, cardboard, etc.), and may protect the nasal device dispensers from damage. For example, the case may be formed of a polymeric material (e.g., a hard plastic), or the like. The case may include a cover that can be opened. The cover may be hinged to the body of the case. In general, a case may be similar to a multi-use dispenser; cases typically refer to containers of packaged units (e.g., a plurality of closed or sealed dispenser housings).

In some variations, a packaging system includes at least one applicator configured to assist in applying an adhesive nasal device. The applicator may be a separate element, or it may be a part of the dispenser or support backing. For example, the support backing may be folded to form an applicator region (e.g., a projection that is at least partially insertable into the subject's nose, allowing the device to be aligned and applied to the nose. In one variation the dispenser housing includes an applicator region that may be used to guide the application of one (or both) nasal devices to the subject's nose.

Also described herein are packaging systems for dispensing adhesive nasal device that include a first nasal device comprising an airflow resistor, a second nasal device comprising an airflow resistor, and a support backing to which the first and second nasal devices are removably secured.

Also described herein are packaging systems for dispensing adhesive nasal devices that include a plurality of adhesive nasal devices (each adhesive nasal device having an airflow resistor and/or an adhesive holdfast), a support backing to which at least one of adhesive nasal device is removably secured, and a dispenser configured to substantially surround the adhesive nasal devices. As mentioned above, the dispenser (or dispenser housing) may be a pouch. The pouch may be paper or foil (e.g. a single-use dispenser) and may include a tear line indicating a location along which the pouch may be opened.

Also described herein are packaging systems for dispensing adhesive nasal devices that include one or a plurality of nasal devices (wherein each adhesive nasal device comprises an airflow resistor as described above), a dispenser housing (wherein the plurality of nasal devices are positioned in the housing), and a lid covering the plurality of nasal devices within the dispenser housing. The nasal devices may be removably secured within the dispenser housing. The lid may be configured to be pulled off of the dispenser housing to expose the plurality of nasal devices. For example, the lid may be a foil or thin plastic material that can be peeled off of the dispenser housing.

Also described herein are packaging systems for dispensing adhesive nasal devices that include at least one adhesive nasal device (wherein the adhesive nasal device comprises an airflow resistor) and a support backing card to which the nasal device is removably secured. The support backing typically includes an opening therethrough, and the airflow resistor of the nasal device is aligned with the opening so that it may be tested after the nasal device is attached to the support backing. The system may also include additional openings (e.g., detachment openings) on the support backing to help facilitate the removal of the nasal device from the support backing.

Also described herein are methods of packaging a plurality of nasal devices. For example, a method of packaging a plurality of nasal devices may include: aligning an airflow resistor of a nasal device with an opening through a support backing, and releasably securing the nasal device to the support backing so that the airflow resistor is aligned with the opening. The support backing and airflow resistor may be sealed within a dispenser housing. The method may also include testing the resistance through the airflow resistor after it has been secured to the support backing. In some variations, the method further includes sterilizing the nasal device in the dispenser housing. The nasal devices may be sterilized separately from the housing and then placed into the sterile housing, or the housing and the plurality of nasal devices may be sterilized together. In some variations, the sterilizing step occurs after the packaging system including the nasal devices has been assembled. The step of sterilizing may involve any appropriate sterilization method, including heat (thermal sterilization), radiation (X-ray sterilization), etc.

Also described herein are methods of packaging a nasal device that includes the steps of removably securing a plurality of nasal devices to a support backing (wherein each nasal device comprises an airflow resistor) and placing the support backing, including the nasal device (or a plurality of devices), within a housing. The housing may then be sealed. The airflow resistor of the nasal device may be aligned with an opening through the support backing. In some variations the airflow resistor (or a portion thereof) passes through the opening.

In some variations, the step of placing the support backing within the housing comprises placing the support backing including the nasal device(s) within a pouch or a tray (e.g., the housing is a pouch or a tray).

Also described herein are methods of packaging one or a plurality of nasal devices including the step of forming the nasal device(s) on or as part of a backing substrate. For example, the method may include the steps of: forming one or a plurality of openings in a backing substrate, applying an adhesive layer to the backing substrate, forming a holdfast region in the adhesive substrate around the opening(s), and securing an airflow resistor in communication with the opening(s). In some variations, the holdfast regions is formed in the adhesive substrate by kiss cutting. The step of securing the airflow resistor to the plurality of holdfast regions may include securing a flap valve to the holdfast region(s). The method may further include the step of packaging the nasal devices. For example, the method may include placing the backing substrate into a dispenser housing (e.g., single-use dispenser such as a tray, pouch or the like, or a multi-use dispenser). The backing substrate (and nasal devices) may then be sealed within the dispenser housing.

INCORPORATION BY REFERENCE

All publications and patent applications mentioned in this specification are herein incorporated by reference in their entirety, to the same extent as if each individual publication or patent application was specifically and individually indicated to be incorporated by reference in its entirety.

BRIEF DESCRIPTION OF THE DRAWINGS

FIG. 10A is a variation of a packaging system including a tray.

FIGS. 10B and 10C are another variation of a packaging system.

DETAILED DESCRIPTION

Figure 1A:
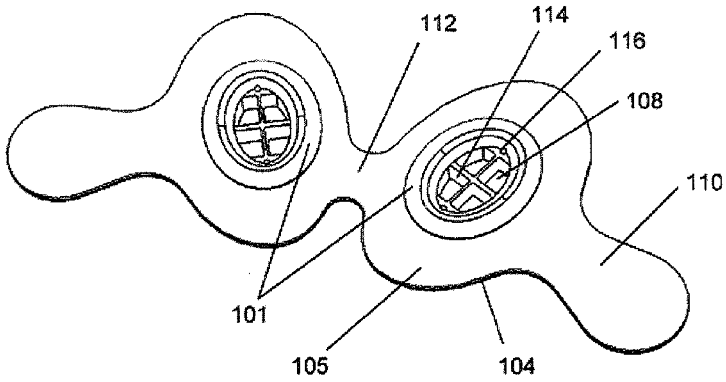
FIGS. 1A and 1B are a bottom and top perspective views, respectively, of one variation of a nasal device.

Described herein are systems and methods for packaging and dispensing nasal devices, including dispensers for dispensing nasal devices. In general, one (or typically more than one) nasal devices are packaged so that the nasal device(s) are removably secured to a support backing. The support backing may be at least partially enclosed in a dispenser housing.

The nasal devices are removably secured to a support backing in any appropriate manner. A device that is removably secured to a support backing may be removed by a user, including a subject that will wear the nasal device once it has been removed. For example, the nasal device(s) may be removably secured through an adhesive. Thus, an adhesive nasal device may be peeled off of the support backing so that the (now exposed) adhesive substrate of the nasal device may be applied to the subject's nose. In some variations, the nasal device is removably secured to the support backing by perforations or other frangible connections to the support backing. For example, the support backing may be a component (e.g., layer) used to form the nasal devices, such as the adhesive backing layer. The nasal device may be partially cut (e.g., through perforations) during the formation of the nasal device.

Nasal devices, support backings, dispensers, and other components that may be included as part of a systems of packaging nasal devices are described in detail in the sections that follow. Methods of packaging nasal devices and methods of dispensing nasal devices are also described below. Although this description may be divided into sections, any of the elements and components described in each of these sections may be incorporated or used with any of the elements and components described in any of the other sections.

In some variations a packaging systems may include a dispenser housing, including single-use and multi-use dispenser housings. Examples of different dispenser housings are provided herein. As used in this specification, the singular forms "a," "an," and "the" include plural reference unless the context clearly dictates otherwise.

Nasal Devices

Any of the packaging systems described herein may be used with any appropriate nasal device, particularly adhesive nasal devices, including those described in more detail in FIGS. 1A to 2B, below.

In general, a nasal device (including an adhesive nasal device) may be secured in communication with a subject's nose, and specifically with one or both of the subject's nasal cavities. A typical nasal device includes an airflow resistor configured to resist airflow in a first direction more than airflow in a second direction, and an adhesive holdfast configured to secure the airflow resistor at least partially over, in and/or across the subject's nose or nostril. The holdfast may include a biocompatible adhesive and a flexible region configured to conform to at least a portion of a subject's nose. The nasal devices described herein are predominantly adhesive nasal devices, however the systems and methods for packaging and dispensing nasal devices may be used with nasal devices that are not adhesive nasal devices.

Adhesive nasal devices may be worn by a subject to modify the airflow thorough one or (more typically) both nostrils. One or more adhesive nasal devices may be secured over both of the subject's nostrils so that airflow through the nostrils passes primarily or exclusively through the nasal device(s). Adhesive nasal devices are removably secured over, partly over and/or at least partly within the subject's nostrils by an adhesive. The adhesive nasal devices described herein may be completely flexible, or partially rigid, or completely rigid. For example, the devices described herein may include an adhesive holdfast region that is at least partially flexible, and an airflow resistor. The airflow resistor may be flexible, or rigid. In some variations, the devices described herein also include one or more alignment guides for helping a subject to orient the device when securing it over the subject's nose. The adhesive nasal devices described herein may be composed of layers. Nasal devices composed of layers (which may also be referred to as layered nasal devices) may be completely or partially flexible, as previously mentioned. For example, a layered nasal device may include an airflow resistor configured to resist airflow in a first direction more than airflow in a second direction and an adhesive holdfast layer. In some variations, the airflow resistor may be a flap valve layer adjacent to a flap valve limiting layer, and may include an adhesive holdfast layer comprising an opening across which the airflow resistor is operably secured. The airflow resistor may be disposed substantially in the plane of the adhesive holdfast layer. The adhesive holdfast layer may be made of a flexible substrate that includes a biocompatible adhesive.

Nasal respiratory devices, including adhesive respiratory devices, may be used to regulate a subject's respiration. For example, a nasal device may create positive end expiratory pressure ("PEEP") or expiratory positive airway pressure ("EPAP") during respiration in a subject wearing the device. The adhesive nasal devices and methods described herein may be useful to treat a variety of medical conditions, and may also be useful for non-therapeutic purposes. For example, a nasal respiratory device may be used to treat sleep disordered breathing or snoring. The systems, devices and methods described herein are not limited to the particular nasal device embodiments described. Variations of the embodiments described may be made and still fall within the scope of the disclosure.

As used herein, an adhesive nasal device may be configured to fit across, partly across, at least partly within, in, over and/or around a single nostril (e.g., a "single-nostril nasal device"), or across, in, over and/or around both nostrils ("whole-nose nasal device"). Any of the features described for single-nostril nasal devices may be used with whole-nose nasal devices, and vice-versa. In some variations, an adhesive nasal device is formed from two single-nostril nasal devices that are connected to form a unitary adhesive nasal device that can be applied to the subject's nose. Single-nostril nasal devices may be connected by a bridge (or bridge region, which may also be referred to as a connector). The bridge may be movable (e.g., flexible), so that the adhesive nasal device may be adjusted to fit a variety of physiognomies. The bridge may be integral to the nasal devices. In some variations, single-nostril nasal devices are used that are not connected by a bridge, but each include an adhesive region, so that (when worn by a user) the adhesive holdfast regions may overlap on the subject's nose.

Layered nasal devices are of particular interest. Layered adhesive nasal devices may include two or more layers. For example, a layered nasal device may include an adhesive holdfast layer and an airflow resistor layer. These layers may be composed of separate layers, and these layers may be separated by other layers, or they may be adjacent. The adhesive holdfast layer may be itself formed of layers (optionally: a substrate layer, a protective covering layer, an adhesive layer, etc), and thus may be referred to as a layered adhesive holdfast. Similarly, the airflow resistor may be formed of multiple layers (optionally: a flap valve layer, a valve limiter layer, etc.), and thus may be referred to as a layered airflow resistor. In some variations, the layered adhesive holdfast and the layered airflow resistor share one or more layers. For example, the flap valves layer and the adhesive substrate layer may be the same layer, in which the leaflets of the flap valve layer are cut from the substrate layer material. As used herein, a "layer" may be generally planar geometry (e.g., flat), although it may have a thickness, which may be uniform or non-uniform in section. As mentioned briefly above, the support backing may be formed of one of the layers of a layered nasal device, such as the adhesive substrate layer.

In some variations, an adhesive nasal device has a body including a passageway configured to be placed in communication with a subject's nasal passage. The body region may be a stiff or flexible body region, and may secure an airflow resistor therein. In some variations, the body region is at least partially surrounded by a holdfast (e.g., a planar adhesive holdfast). The body region may be modular, meaning that it is formed of two or more component sections that are joined together.

In some variations, the adhesive nasal device may further include a support frame. The support frame may provide structural support to all or a portion of the nasal device, such as the flexible adhesive portion. For example, the support frame may support the adhesive holdfast portion of the device and be completely or partially removable after the device has been applied to the subject. In some variations, the support frame remains on the nasal device after application. In some variations, the support frame is a support frame layer.

An adhesive nasal device may also include a tab or handle configured to be grasped by a subject applying the device. In some variations, this tab or handle is formed of a region of the layered adhesive holdfast.

The various components of the device may be made of any appropriate materials, as described in greater detail below. For example, some device components (e.g., an alignment guide, a body region) may be made of medical grade plastic, such as Acrylonitrile Butadiene Styrene (ABS), polypropylene, polyethylene, polycarbonate, polyurethane or polyetheretherketone. The airflow resistor may be a flap valve and the flap may be made of silicone or thermoplastic urethane. The adhesive holdfast may include an adhesive substrate made of silicone, polyurethane or polyethylene. Examples of biocompatible adhesive on the adhesive holdfast may include hydrocolloids or acrylics.

In some versions, the nasal device further comprises an active agent. In some versions, this active agent is a drug (e.g., a medicament). In some versions, this active agent comprises an odorant, such as a fragrance. In some versions, the active agent comprises menthol, eucalyptus oil, and/or phenol. In other versions, the nasal device may be used with other pulmonary or medical devices that can administer medication or other medical treatment, including, but not limited to, inhalers and nebulizers.

A nasal device may include a filter. This filter may be a movable filter, such as a filter that filters air flowing through the passageway in one direction more than another direction (e.g., the device may filter during inhalation but not expiration).

As mentioned, the adhesive nasal devices described herein typically include a holdfast region (or layer) and at least one airflow resistor. As will be apparent from the figures, many of these devices may be removable and insertable by a user without special tools. In some variations, a subject may use an applicator to apply the device (e.g., to help align it). FIGS. 1A through 2B illustrate different exemplary nasal devices.

Figure 1B:
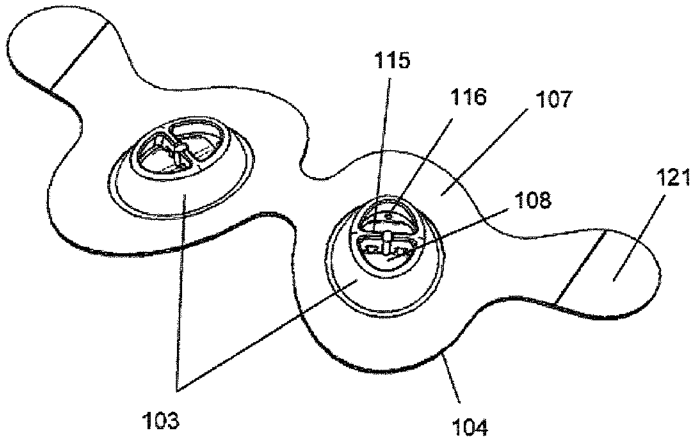

FIGS. 1A and 1B show perspective views of one exemplary variation of an adhesive nasal device as described herein. FIG. 1A shows a front perspective view of an adhesive nasal device, looking at the "outer" side of the device, which is the side facing away from the subject's nose when the device is worn. The device shown in FIG. 1A includes two single-nostril rim bodies 101 and a single adhesive holdfast 104. A nasal device may be configured to communicate with a single nostril (a single-nostril nasal device), or it may be configured to communicate with both of a subject's nostrils (a whole-nose nasal device). The nasal device illustrated in FIGS. 1A and 1B is configured to communicate with both of a subject's nostrils.

A holdfast 104 (which adhesively secures the device to the subject) is shown as a layered structure including a backing or adhesive substrate 105. This backing may act as a substrate for an adhesive material, or it may itself be adhesive. The holdfast 104 may have different regions, including two peri-nasal regions surrounding the rim bodies 101. Each rim body has at least one passageway 108 for airflow therethrough. The adhesive holdfast also includes two tabs or grip regions 110 that may make the device easier to grasp, apply, and remove. A bridge region 112 is also shown. In this example, the bridge region is part of the adhesive holdfast (e.g., is formed by the same substrate of the adhesive holdfast) and connects the peri-nasal regions. Although the tab and bridge regions are shown as being formed as part of (integral with) the holdfast material, these regions may also be formed separately, and may be made of different materials.

The rim body regions 101 shown in the exemplary device of FIG. 1A include outer rim body regions which each encompass a passageway 108. These first (e.g., outer) rim body regions may mate with a second (e.g., inner) rim body regions to form the rim body region(s) of the device that includes the passageway 108. These passageways in this example are interrupted by crossing support members 114 (e.g., cross-beams or cross-struts) that may partly support or restrict movement of the airflow resistor. In addition, each rim body region 101 includes two leak pathways 116, through which air may pass even when the passageway through the device is otherwise blocked by the airflow resistors. The leak pathways 116 are shown here as small openings at the narrow ends of the oval-shaped outer rim body region. The rim body region may also be referred to as 'rim' or 'scaffold' regions of the device.

FIG. 1B shows a back perspective view of the opposite side of the adhesive nasal device shown in FIG. 1A, the "inner side" of the device. The inner side of the device faces the subject, and a portion of this side of the device may contact the subject. This side of the device, and particularly the adhesive holdfast of the device, includes an adhesive (which may be covered by a protective cover 107) forming part of the holdfast 104. In some variations, the entire skin-facing side of the holdfast 104 includes an adhesive on the surface, although in some variations, only a portion of this region includes adhesive. The adhesive may be a distinct layer of the holdfast (e.g., it may be layered on top of an adhesive substrate), or it may be an integral part of the holdfast (e.g., the adhesive substrate may be made of an adhesive material). In some variations an adhesive may be separately added to the device (e.g., the holdfast region) before use. The adhesive material may be covered by a removable protective cover or liner 107, to prevent the adhesive from sticking to surfaces until after the liner is removed. In FIG. 1B, the protective cover 107 covers the entire skin-facing surface of the holdfast. The device may be applied by first removing the liner. For example, the liner may be peeled off, to expose the adhesive. In some variations, the liner protecting the adhesive may be partially removed. For example, the tab region 121 of the device may include a separate (or additional) liner that remains over the tab region when other liner regions are removed. This may allow the device to be held by the tab region without having it adhere to the skin. After removing the cover, or a part of the cover, the device may be positioned and adhered to the subject's skin around the nasal cavity, so that the passageways through the rim body are aligned with the openings of the subject's nasal cavities. In some variations, an additional adhesive cover region (e.g., the protective cover region over the tabs 121) can then be removed to secure the device to the rest of the subject's nose. The adhesive cover may include a fold (or crimp, crease, lip, or the like) that helps to remove the protective cover from the adhesive. All or a portion of the adhesive cover may also be left on the device as it is worn, and may help remove the device after use.

The second, or inner, rim body region 103 shown in the exemplary device of FIG. 1B is shaped with an inwardly-tapering edge, so that it may fit at least slightly within the opening of the subject's nostril when a subject wears the device, which may help guide the application of the device (e.g., this rim may serve as an alignment guide). The inner rim body includes one or more passageways 108 that correspond with the passageways 108 shown in FIG. 1A. Similarly, the leak pathways pass completely through the rim body (both inner and outer bodies). The tapering external walls of the inner rim body region(s) shown in FIG. 1B are shown as smooth, and may also include an additional material (e.g., an auxiliary holdfast material) for securing them in the subject's nostrils, or for cushioning them to prevent injury or discomfort. These surfaces may also be more or less angled, in order to facilitate comfort when the adhesive nasal device is worn in the subject's nose. A cross bar (region 115) may also be provided as part of the inner rim body. The inner rim body 103 may extend some distance above the peri-nasal annular region of the holdfast, as shown in FIG. 1B. This distance may be sufficient to prevent any portion of the airflow resistor (e.g., a flap portion of a flap valve) from extending out of the device and into the nasal cavity where is might contact body tissues (including hairs).

Figure 2A:
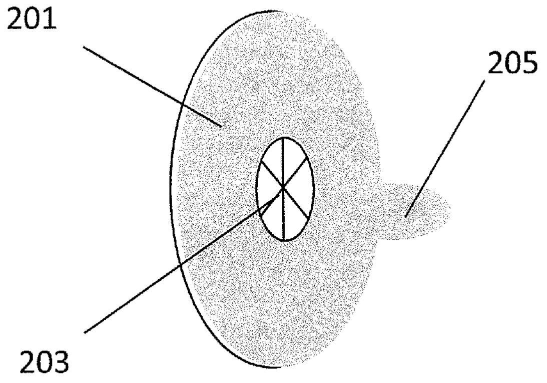
FIGS. 2A and 2B show one variation of a layered nasal device in a top view and an exploded perspective view, respectively.
Figure 2B:
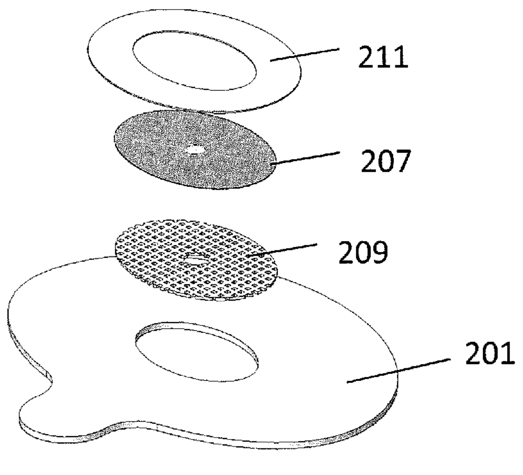

FIG. 2A is a top view of another example of a nasal device. The nasal device shown in FIGS. 2A-2B is a layered nasal device that includes a holdfast layer 201 and an airflow resistor 203. The reverse side of the device shown in FIG. 2A includes an adhesive material (not shown) that may be covered by a protective covering. The protective covering (which may also be referred to as a protective liner) can be removed to expose the adhesive before or during application of the device. Thus, the holdfast layer of the device secures it to the subject. This holdfast layer may itself be layered, and may include an adhesive substrate (e.g., a backing layer). For example, the adhesive substrate may be a foam backing. This backing may act as a substrate for an adhesive material. In some variations, the adhesive substrate is itself adhesive. The holdfast layer 201 may have different regions, including a peri-nasal regions surrounding an opening (though which air may flow), and a tab 205 or grip region forming a tab that may make the device easier to grasp, apply and remove. Other regions may include regions of more aggressive and less aggressive adhesive (e.g., more or less adhesive material), regions of hydrogel material (including adhesive hydrogels) to help prevent irritation from repeated or extended use. Although the tab is shown as part of (integral with) the holdfast material, this region may also be formed separately, and may be made of different materials.

FIG. 2B shows an exploded view of the device of FIG. 2A. This exploded perspective view illustrates the layers of the device, including the adhesive holdfast 201 (which may itself be layered), two layers of airflow resistor, including the flap valve 207 and flap valve limiter 209, and an adhesive ring 211 that may help attach the flap valve and flap valve limiter to the adhesive holdfast.

An adhesive holdfast for a nasal device may comprise any appropriate material. For example, the adhesive substrate may be a biocompatible material such as silicone, polyethylene, or polyethylene foam. Other appropriate biocompatible materials may include some of the materials previously described, such as biocompatible polymers and/or elastomers. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Structurally, the substrate may be a film, foil, woven, non-woven, foam, or tissue material (e.g., poluelofin nonwoven materials, polyurethane woven materials, polyethylene foams, polyurethane foams, polyurethane film, etc.).

In variations in which an adhesive is applied to the substrate, the adhesive may comprise a medical grade adhesive such as a hydrocolloid or an acrylic. Medical grade adhesives may include foamed adhesives, acrylic co-polymer adhesives, porous acrylics, synthetic rubber-based adhesives, silicone adhesive formulations (e.g., silicone gel adhesive), and absorbent hydrocolloids and hydrogels.

Support Backing

The support backing typically supports a plurality of nasal devices, allowing them to be readily dispensed. The support backing may also protect the devices, particularly the holdfast region and the airflow resistor. For example, the support backing may be configured to limit movement of the airflow resistor (e.g., flap valve) until the device is dispensed by removing it from the support backing. In general, the support backing provides a surface or shape to which the nasal device(s) may be removably attached.

The support backing may be any appropriate material, and may particularly include at least one surface to which the nasal devices may be attached and later dispensed. For example, in some variations, the support backing includes an attachment surface (for removably attaching the nasal devices) that will releasably attach to all or a portion of the adhesive substrate of a nasal device. For example, the support backing may include an adhesive substrate to which the adhesive nasal device is removably affixed. This adhesive substrate may be a substantially non-stick surface (including some hydrophobic surfaces, including silicone). The support backing may be a smooth and/or non-stick (e.g., siliconized) surface permitting removable attachment to the adhesive nasal device. To remove an adhesive nasal device from the support backing, a subject can pull or peel the adhesive nasal device from the support backing. In some variations, the support backing is a frangible material from which a connected device may be detached. For example, the device may be connected to the nasal device by perforations or other frangible connections. Thus, a subject may apply force to release a nasal device from the support backing to tear the perforations or the support backing. In some variations, the support backing includes a material (e.g., an adhesive, gel, etc.) that may be removed or dissolved by applying a solvent (e.g., water) to release an attached nasal device. Removing the adhesive nasal device from the support backing may expose all or a portion of the adhesive holdfast of the nasal device so that it can be secured to a subject.

The support backing may be formed of (or include) any appropriate material that releasably holds the nasal devices secure until they are dispensed. In some variations the support backing is a material such as a paper, fabric, plastic, metal foil, or the like. In particular, materials that may be formed thin (e.g., as sheets) may be useful. Polymeric materials are of particular interest. The surface of the support backing to which the adhesive nasal device attaches may be treated so that the nasal device may be readily released. As mentioned, the support backing may include a surface that allows the adhesive holdfast of the nasal device to be removed so that the adhesive can then be applied to the skin. In some variations, the support backing has a substantially hydrophobic surface (e.g., a wax coating).

The support backing may be formed in any appropriate shape. For example, the support backing may be formed in a substantially flat shape (e.g., a sheet, a roll, a card, etc.). The support backing may be formed in a thin, substantially flat shape that can be rolled, cut and/or folded. The final shape of the support backing may be matched to the dispenser, as described in more detail below (e.g., roll dispenser, etc.). In some variations, the support backing is formed from a component of the layers used to form the nasal device.

FIGS. 3A to 4B illustrate different variations of support backings to which adhesive nasal devices have been attached. For example, FIG., 3A shows a perspective view of a rolled support backing 301 to which a plurality of nasal devices 305, 305' are attached. The roll may include numerous nasal devices. Nasal devices may be dispensed from the roll, as described in more detail in FIG. 11A, below.

Figure 3A:
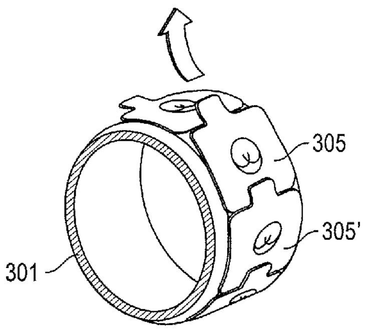
FIGS. 3A to 3D show variations of packaging for adhesive nasal devices.
Figure 3B:
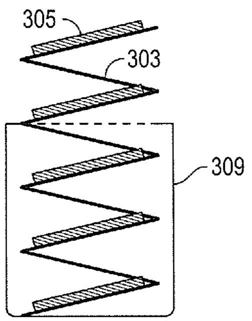

FIG. 3B shows a cross-sectional view of a support backing that is configured as a folded stack 303 of nasal devices 305. Each nasal device 305 in the stack is attached to the support backing, and may be individually peeled (or otherwise removed) from the support backing. The support backing and attached nasal devices may therefore be placed in a stack (e.g., a vertical stack), and individually removed. This variation may be used with a stack dispenser 309.

Figure 3C:
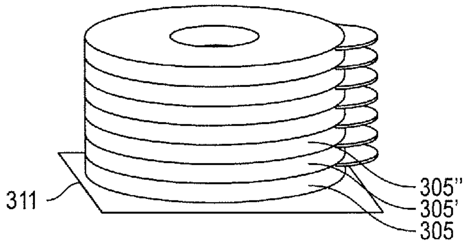

FIG. 3C shows another variation of a support backing, in which only one of the stack of nasal devices 305 is attached directly to the support backing 311. In this example, the support backing is shown as a flat square, however the support backing may be the same dimension as the nasal device (e.g., oval or round). Although only the bottom nasal device 305 is attached to the support backing, additional nasal devices 305', 305" are each attached to adjacent nasal devices. For example, the penultimate nasal device 305' (adjacent to the bottom nasal device 305) is attached to the top of the bottom nasal device, which is in turn attached to the support substrate. Nasal devices may be dispensed by (for example) peeling them off from each other, and eventually from the support backing. Dispensers for stacked nasal devices are described in FIGS. 12A-17C, below.

Figure 3D:
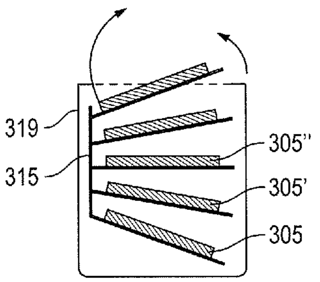

FIG. 3D is a cross-sectional view through another variation of a stack of nasal devices 305, 305' attached to a support backing 315, in which each nasal device in the stack is attached to the support backing 315. In this variation, the support backing includes projections (e.g., "shelves") onto which nasal devices are releasably attached. As the nasal devices are removed, the shelf of the support backing may also be removed (e.g., by tearing, etc.), or otherwise moved out of the way. Although FIG. 3D shows the support backing and attached nasal devices fanned out, they may be stacked to resemble the nasal devices shown in FIG. 3C. Dispensers for this type of nasal device support backing 329 may resemble the dispensers shown in FIGS. 12A-17C.

Figure 4A:
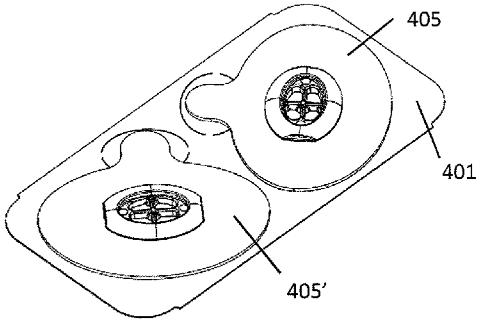
FIG. 4A is a top perspective view of one variation of a packaging system.
Figure 4B:
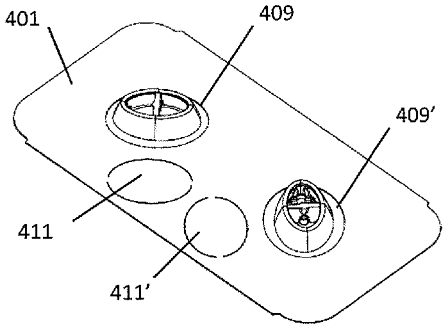
FIG. 4B is a bottom perspective view of the packaging system of FIG. 4A.
Figure 5A:
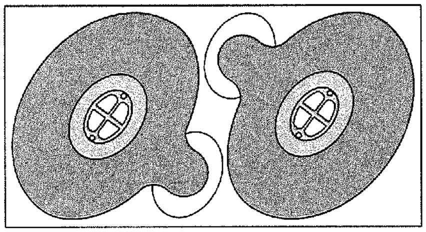
FIGS. 5A-5D are variations of packaging systems.
Figure 5B:
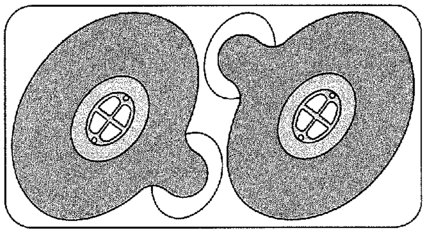
Figure 5C:
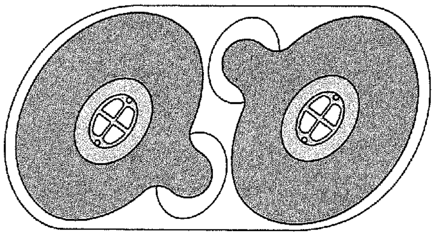
Figure 5D:
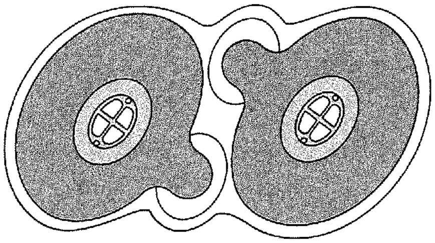

In some variations, the support backing for the nasal devices is configured as a card or sheet. For example, FIGS. 4A-4B show a variation in which two nasal devices 405, 405' are releasably attached to a card 401. The support backing (card, in this example) may be made of a stiff or rigid material, such as cardboard or thin plastic. The card is sized so that two nasal devices may be positioned on the surface. For example, this card is less than 5 inches in diameter by less than two inches in width. Thus, the card may be wallet- or pocket-sized. FIG. 4A, shows a pair of nasal devices 405, 405' attached (by their adhesive holdfast regions) to the card. FIG. 4B shows the back side of the card. In this example, the card includes four cut-out regions, two of which are holes or openings. Two openings 409, 409' are configured so that a portion of a nasal device (in this case, the inner rim body region) passes through the card. The second pair of cut-out regions 411, 411' is positioned to more easily allow access to the tabs regions of the each nasal device. The second cut-out regions may be openings (e.g., completely cut out) or they may be perforations or incompletely cut-out. These second cut-out regions 411, 411' may be called grip openings or grip cutouts, that help a subject grasp and remove the nasal device from the card. In this example, the nasal device tab regions may be grasped from the openings, and these tabs can be used to help peel each nasal device off of the card. In some variations the grip openings are cut or perforated, but not removed. A subject may push open the grip openings (e.g., by applying pressure from beneath) and then grasp the tab.

In general, the card may be shaped or configured in any appropriate manner and the nasal devices may be organized in any appropriate manner. For example, in FIGS. 4A and 4B the pair of nasal devices are arranged on the same side of the card, and are side-by-side, with the tab region of the nasal device arranged along one side of the card. In some variations, the nasal devices may be on opposite sides of the card, and/or the nasal devices may be arranged in different orientations. In some variations, "handed" nasal devices may be used and packaged by releasably attaching them to a support backing. For example, a "left" nasal device and a "right" nasal device may be positioned on the same card.

FIGS. 5A to 5D illustrate additional examples of support backings that are configured as cards for holding a pair of nasal devices. For example, in FIG. 5A the nasal devices are arranged side-by-side on a square card. In some variations, the card may include rounded edges, as shown in the various embodiments shown in FIGS. 5B-5D.

Figure 6A:
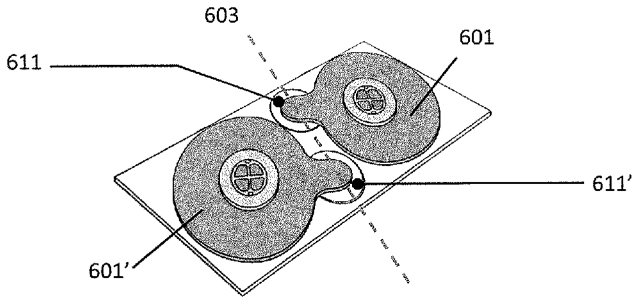
FIG. 6A is another variation of a packaging system.
Figure 6B:
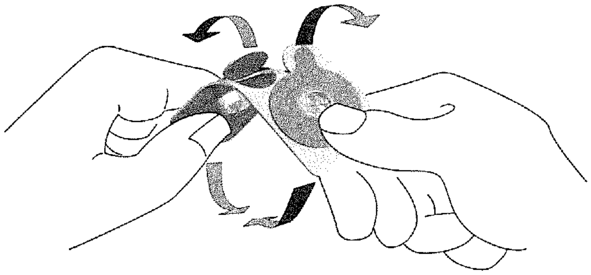
FIG. 6B illustrates the operation of the packaging system of FIG. 6A.

In some variations, the support backing includes a bend axis. The bend axis may be marked or pre-creased, or scored to indicate where the card may be bent or folded. In some variations this bend axis may be used to help remove the nasal devices from the card. An example of this is shown in FIGS. 6A and 6B. In FIG., 6A, a pair of nasal devices 601, 601' are arranged side-by-side on a support backing configured as a card. Each nasal device includes a tab region for helping to manipulate the nasal device, including helping to remove the nasal device by peeling it off of the support backing. As mentioned above, a grip opening 611, 611' is located below each of the tabs. These grip openings are not removed, but are at least partially cut out. In FIG. 6A, the dotted line 603 indicates the bend axis. In some variations, this dotted line is indicated on the support backing itself. For example, the support backing may include a line drawn on it, or a crease, groove, or other marker indicating a bend axis.

FIG. 6B illustrates the operation of the bend axis of a support backing. By bending the card along the bend axis 603, the card is bent or flexed and the tab regions of each nasal device are made to project slightly from the surface of the card. The tab regions may then be grasped and used to remove the nasal devices from the card. In this example, the tab region is still attached to the grip opening that is cut from the card (but not removed). In some variations the grip opening is completely removed. In other variations, the grip opening is not removed, but is merely perforated or partially cut out.

Figure 6C:
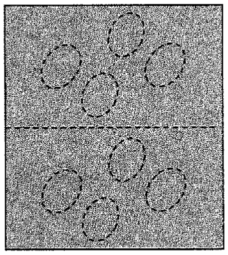
FIGS. 6C and 6D illustrate one variation of a method for forming the packaging system shown in FIG. 6A.
Figure 6D:
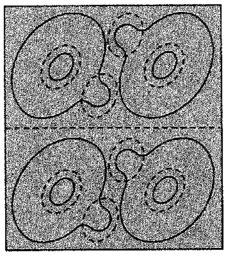

FIGS. 6C and 6D illustrate a support backing that is configured as a sheet. The support backing is similar to the card variation shown in FIGS. 6A and 6B, but includes four nasal devices, rather than just two nasal devices. This variation may also be referred to as a card, and the card may be folded or cut along the horizontal lines indicated.

Figure 7A:
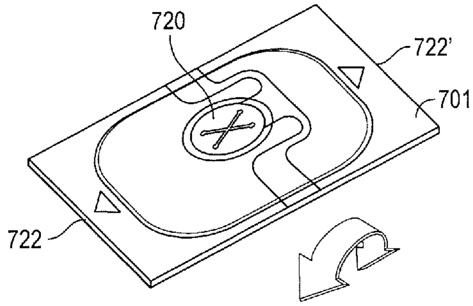
FIGS. 7A-7C illustrates the operation of one variation of a packaging system as described herein.
Figure 7B:
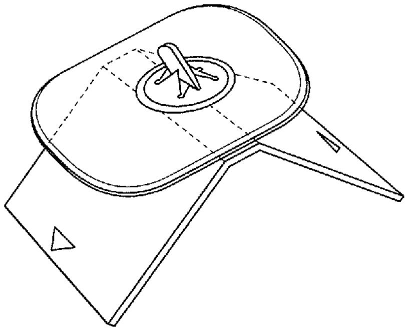
Figure 7C:
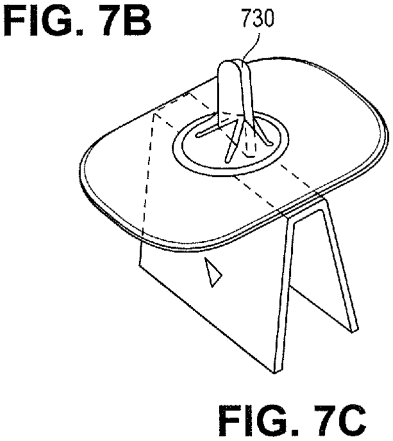

Some variations of the systems for dispensing nasal devices described herein may include one or more applicators. An applicator may be used to apply a nasal device to a subject's nose. For example, a nasal device may be placed on an applicator, and the applicator can be grasped by the subject to position and attach the nasal device on, over, or across the subject's nostril. In some variations the applicator is an integral part of the dispenser (e.g., the dispenser housing). In some variations the applicator is a separate component that is included or packaged with the plurality of removably linked nasal devices and the support backing. In some variations the applicator is an integral part of the support backing. FIGS. 7A-7C illustrate an applicator that is formed by the support backing.

FIG. 7A illustrates a single nasal device 705 that is removably connected to a support backing 701. Although this example includes only a single nasal device, variations in which multiple nasal devices are attached to the same support backing are also contemplated. In this example, the support backing includes multiple bend axes (creases) as well as arrows 722, 722' indicating where the support backing can be bent to form the applicator, as shown in FIGS. 7B and 7C.

Bending the support backing 701 to move the ends of the support backing down (as shown by the arrow in FIG. 7A), moves the support backing away from the nasal device (e.g., the holdfast region of the nasal device), and causes an alignment guide, post 730 to extend through the airflow resistor 720, as shown in FIGS. 7B and 7C. In some variations, an alignment guide 730 does not extend from the support backing 701. In other variations the alignment guide is part of the nasal device (e.g., the inner body rim in FIG. 1A). In FIG. 7C the two ends of the support backing that are folded together 722, 722' may be used as a handle that can be grasped to help insert the nasal device. In this example the adhesive surface of the adhesive holdfast faces up, away from the support backing, and the nasal device may be connected to the support backing by an adhesive or other removable linkage.

Figure 8:
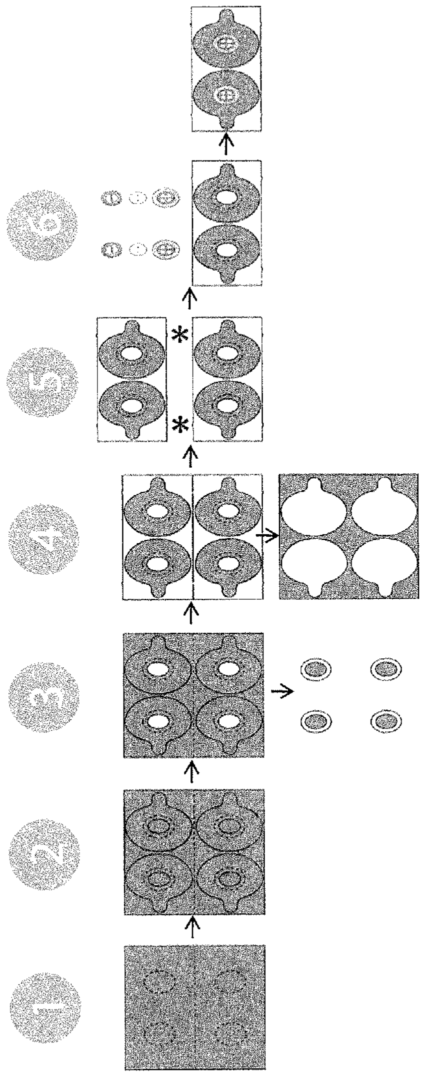
FIG. 8 illustrates one method of manufacturing a packaging system for a plurality of nasal devices.

As mentioned above, nasal devices may be removably attached to a separate support backing, or a nasal device may be formed at least partially from the support backing material. For example, the support backing may be formed as part of a layer of an adhesive device. FIG. 8 illustrates one method of packaging a plurality of nasal devices that includes forming the nasal devices at least partially from the backing support backing material (backing substrate). In FIG. 8 step 1, a layer of support backing is cut (e.g., by "Kiss" cutting) to perforate the support backing. The support backing may also be referred to as a backing substrate. Prior to cutting the support backing, an adhesive may be applied to the front of the support substrate. A removable adhesive cover (e.g., a peel-off adhesive liner, such as Kraft paper) may also be applied over the outer adhesive layer. In step 2 the adhesive on the front of the support backing (and any cover layer) is also kiss cut to form the outline of the adhesive holdfast regions. The center chads are removed in step 3, leaving central openings, as shown. In step 4 the excess adhesive is removed from around the cut adhesive holdfast regions. In optional step 5 individual 'cards' may be formed by separating the backing substrate, as shown. Finally, in step 6 the central airflow resistor is assembled in the central opening. In this example, the airflow resistor is formed by securing an upper rim body and a lower rim body with a flap valve held between them, similar to the embodiment shown in FIGS. 1A and 1B.

Thus, a method of packaging a plurality of nasal device may involve forming a plurality of openings in the backing substrate, applying an adhesive layer to the backing substrate, forming a plurality of holdfast regions in the adhesive substrate, and securing an airflow resistor in communication with each of the plurality of openings.

Dispenser

Any of the nasal device packaging systems described herein may also include a dispenser from which nasal devices may be dispensed and then applied to a subject. A dispenser may (at least partially) surround and protect a plurality of nasal devices, particularly nasal devices that are removably secured to a support backing. Nasal device dispensers can be used to meter the dispensing of nasal devices (e.g., providing a user with a single "dose" of nasal devices). As mentioned, dispensers may also include an applicator or alignment guide.

In some variations, a nasal device dispenser includes a dispenser housing that at least partially surrounds a plurality of nasal devices. The dispenser housing may be made of any appropriate material, including paper, foil, plastics (e.g., polymers), and the like. Dispensers may be formed in any appropriate shape, and may include gripping regions (e.g., handles, etc.). In some variations, the dispenser is configured to be secured to a subject's bed or tabletop.

A dispenser may be a single-use dispenser, or a multi-use dispenser. A single-use dispenser typically stores and dispenses a single "dose" (e.g., a pair of adhesive nasal devices each having an airflow resistor). A single-use dispenser may be sterilized or sterilizable, so that the nasal device can be kept sterile until immediately prior to use, the dispenser is activated (e.g., by opening the dispenser housing). Examples of single-use dispensers include packets, pouches, trays, and the like. Many single-use dispensers include only two nasal devices (or a single nasal device configured to communicate with both nasal passages).

A multi-use dispenser typically includes multiple (e.g., more than two) nasal devices and may be a continuous dispenser. For example, a multi-use dispenser may be used to deliver one or more nasal devices at a time, until the supply of nasal devices (e.g., all of the nasal devices within the dispenser housing) are exhausted. A multi-use dispenser may be reusable or reloadable, so that after all of the plurality of nasal devices initially loaded into the dispenser have been used, additional nasal devices (e.g., nasal devices removably attached to a support backing) can be added to the dispenser. Examples and illustrations of various embodiments of both single-use and multi-use dispenser are described below.

Figure 9A:
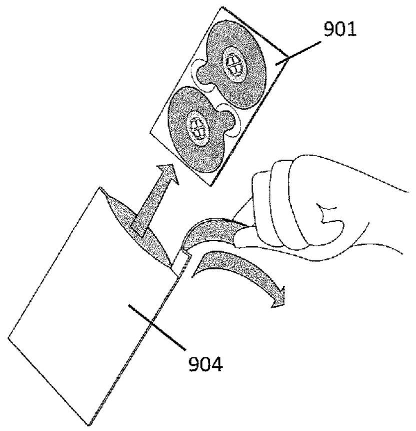
FIGS. 9A and 9B show a packaging system for dispensing nasal devices.
Figure 9B:
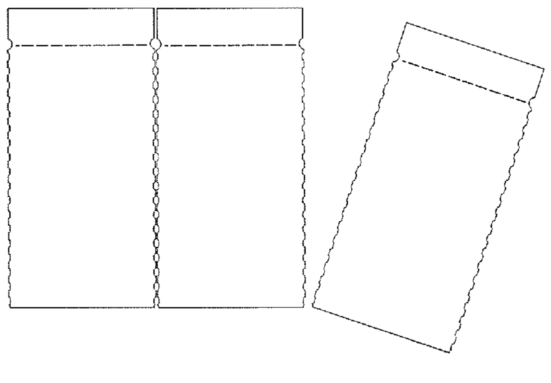

For example, FIGS. 9A and 9B show one variation of a single-use dispenser configured to dispense a pair of nasal devices releasably attached to a support backing card 901. In FIG. 9A the nasal devices are releasably attached to a card 901 (similar to the variation shown in FIG. 5A). This variation of a dispenser includes a dispenser housing 904 that is configured as a pouch. The pouch in this example is made of a lightweight, thin material (e.g., paper, foil, plastic, etc.). The dispenser housing may be sealed around the nasal devices and support backing.

The nasal devices may be dispensed by tearing open the dispenser housing, as illustrated in FIG. 9A. In some variations, the dispenser housing includes a tear line along which the dispenser can be opened (or suggesting to the subject where the dispenser should be opened). The tear line may be a crease, perforation, pull thread, or the like. After opening the dispenser housing, the card containing the nasal devices may be removed.

Any of the dispensers described herein may include drawings, writing, or other instructions for use on the dispenser. For example, the dispenser may indicate how to open and operate the dispenser, how to apply the nasal devices, expiration dates for the nasal devices, identifying characteristics of the nasal device, and/or indications for use of the nasal devices.

In some variations, multiple dispensers may be packaged together, as indicated in FIG. 9B. In this example, multiple single-use dispensers are connected together, and individual dispensers may be removed by separating a dispenser housing from the adjacent dispensers. In some variations (shown and described below in FIGS. 20-22), multiple dispensers may be contained in a case.

FIG. 10A illustrates another variation of a single-use dispenser for dispensing a pair of nasal devices. In this variation, the dispenser housing is configured as a tray in which a pair of nasal devices that are releasably attached to a support backing sits. The tray is covered by a lid or cover 1001 that can be sealed over the tray, and removed (e.g., by peeling it off), as shown in FIG. 10A. For example, the dispenser housing may be a plastic tray that is covered by a foil lid that can be peeled off to expose and dispense the pair of nasal devices on the card. In some variations, the support backing to which the nasal devices can be releasably attached is a part of the dispenser housing. For example, the support backing may be the bottom of the tray shown in FIG. 10A.

FIG. 10B illustrates another variation of a single-use dispenser in which the support backing is also part of the dispenser housing. In FIG. 10B, the dispenser housing is a pouch formed by sealing the edges of a cover 1001' to the edges of a bottom layer 1003. The bottom layer may be the support backing, or it may be a separate component against which the support backing and the nasal devices rest. The nasal devices may be dispensed by separating the cover 1001' from the bottom layer 1003, as shown in FIG. 10C.

Figure 11A:
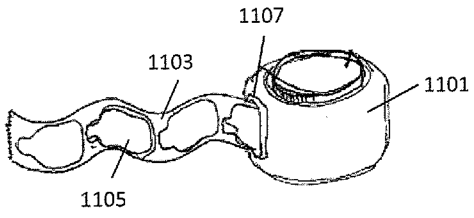
FIGS. 11A to 11C illustrate dispensers for adhesive devices on a rolled support backing.
Figure 11B:
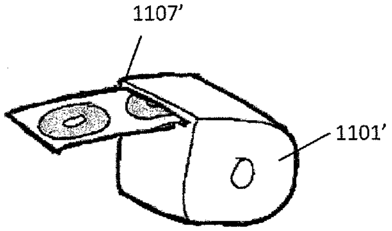
Figure 11C:
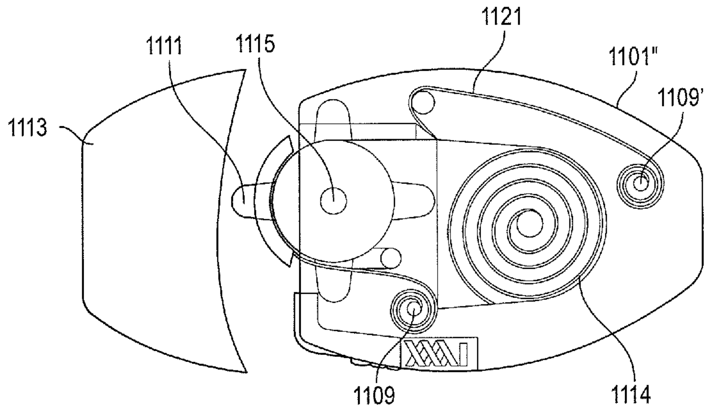

FIGS. 11A-11C show variations of a multi-use dispenser for dispensing nasal devices that are releasably attached to a support backing configured as a roll. In FIG. 11A, the dispenser includes a cylindrical dispenser housing 1101 having an opening 1107 from which the support backing 1103 and nasal devices 1105 may be withdrawn. Individual nasal devices may be removed from the support backing and use, and the support backing may be torn off. In some variations the dispenser also includes a cover or lid that covers the opening 1107. FIG. 11B is another variation of a dispenser, similar to the dispenser shown in FIG. 11A.

FIG. 11C is a transparent view of another nasal device dispenser for use with a roll of nasal devices. In this variation, the dispenser includes a return 1109 for the support backing within the dispenser housing 1101", so that as nasal devices are dispensed from the roll 1114, the support backing is fed back into the dispenser housing and rolled back up on to the return spindle 1109, and does not need to be torn off. This variation also includes an applicator 1111. The applicator in this example projects from the dispenser through the nasal device (e.g., the center passageway of the nasal device, through the open airflow resistor). The applicator may be inserted into the nostril to center the nasal device. The applicator is part of an applicator spindle 1115 that can be rotated to help move the applicators into position for application.

The variation shown in FIG. 11C also peels off the protective support backing (in this example, the support backing is the protective cover or liner) over the adhesive holdfast 1121 and store it in the dispenser hosing 1101" on a second return spindle 1109'. Thus, in this variation the roll of nasal devices may include a continuous support backing on one side and a continuous adhesive cover on the other side, and both the adhesive cover and the support backing are automatically removed by the applicator as the devices are applied. For example, the return spindle and applicator spindle 1115 may be geared to move together and may be controlled by a button, crank, lever, or the like. This control may be located on an outer surface of the housing. The dispenser shown in FIG. 11C also includes a cover 1113.

Figure 12A:
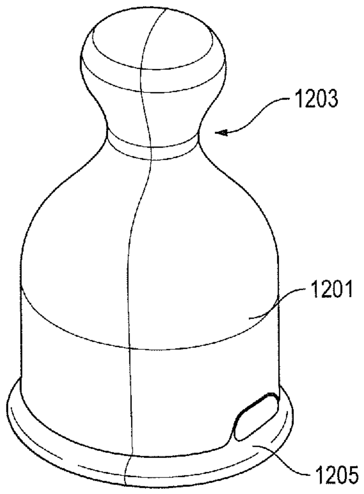
FIG. 12A is a perspective view of a dispenser for a stack of adhesive nasal devices.
Figure 12B:
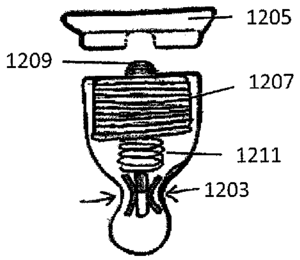
FIG. 12B is a cross-sectional view of the dispenser shown in FIG. 12A.
Figure 12C:
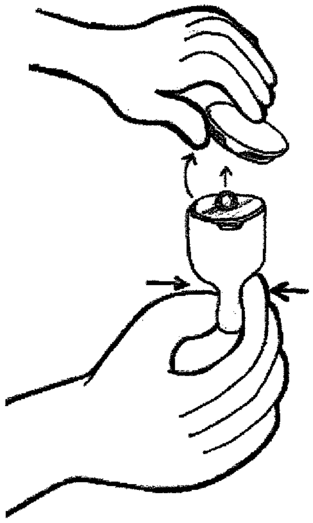
FIG. 12C illustrates operation of a dispenser such as the one shown in FIG. 12A.

FIG. 12A-12C shows another variation of a dispenser including an applicator/aligner. In FIG. 12A the dispenser housing 1201 includes a grip region 1203 at the proximal end. A cover 1205 protects the applicator and nasal devices, as shown in more detail in FIG. 12B. In FIG. 12B the dispenser housing has been made transparent, showing the stack of nasal devices 1207 and the aligner 1209 that can be used to align and apply each nasal device to the subject's nose. The nasal devices in this example may have an adhesive cover over each adhesive layer (not shown), that can be individually removed (e.g., peeled off) before applying. In some variations the nasal devices do not include an adhesive cover, and the adhesive layer for the next nasal device is exposed as the nasal device immediately above it is applied. The dispenser may also include a bias 1211 (e.g., a spring) or other mechanism of advancing the stack of nasal devices as they are dispensed. For example, a pusher may be manually advanced. The dispenser may include stops so that the stack is advanced out of the housing only one nasal device at a time.

The distal end of the housing may act as an applicator. The aligner (post 1209) projects slightly from this distal end, and can be inserted slightly into the subject's nose to help align the nasal device as it is applied. The aligner post 1209 passes through a portion of the nasal device, such as the airflow passageway, by displacing the airflow resistor in the airflow passageway. In some variations the aligner is divided so that it can pass around a valve limiter (e.g., a flap valve limiter). When not in use, the distal end of the applicator may be covered by cover 1205. The cover may be removable or may stay attached (e.g., may be hinged) to the housing when opened.

Figure 13:
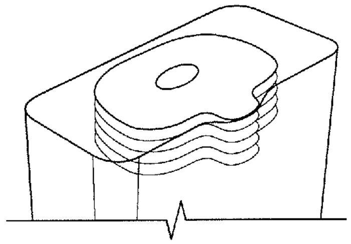
FIG. 13 is a perspective view of a dispenser for a stack of adhesive nasal devices.

FIG. 13 shows the distal end of another variation of a dispenser housing in which a stack of nasal device are secured. This variation does not include a post aligner.

Figure 14A:
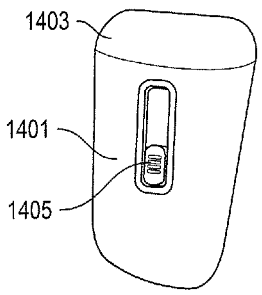
FIGS. 14A and 14B are perspective views of a dispenser (in an open and closed position, respectively).
Figure 14B:
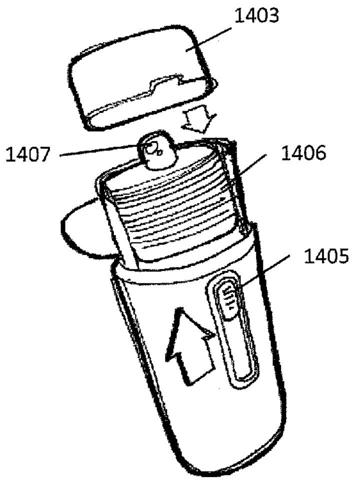

FIGS. 14A and 14B illustrate another variation of a dispenser for a stack of nasal device, similar to the dispenser sown in FIG. 12A-12C. In FIG. 14A the dispenser housing 1401 is shown, and a lid or cap 1403 covers the nasal devices. The cap has been removed in FIG. 14B, revealing the stack of nasal devices 1406 and an aligner 1407. In this example, the nasal devices may be advanced by moving the slider 1405 distally, as shown in FIG. 14B. This variation may also be reloaded with nasal devices by inserting another stack of nasal devices after dispensing all of the initially loaded nasal devices.

Figure 15A:
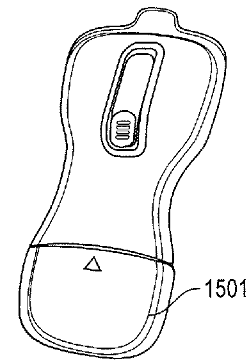
FIGS. 15A and 15B are perspective views of dispensers.
Figure 15B:
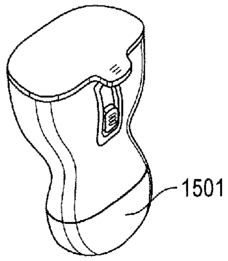

FIGS. 15A and 15B show another variation of the dispenser shown in FIGS. 14A and 14B. In this variation the dispenser housing includes a storage compartment 1501 in the proximal end for storing additional nasal devices.

Figure 16A:
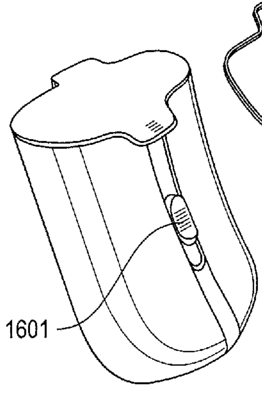
FIGS. 16A-16C are perspective views of another variation of a dispenser.
Figure 16B:
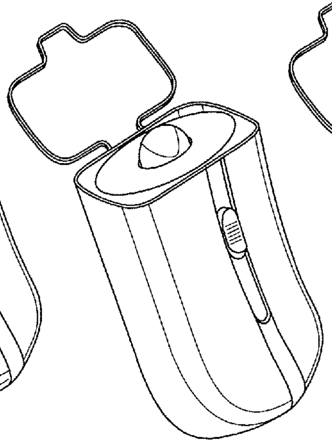
Figure 16C:
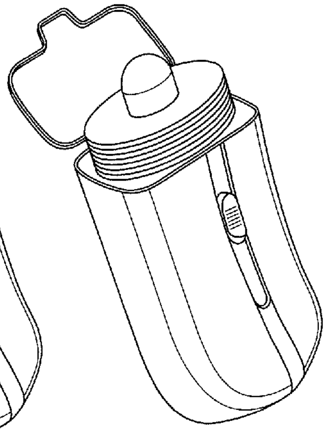

FIGS. 16A-16C illustrate advancing the stack of nasal devices by moving the slider 1601 in a dispenser similar to that described above in FIG. 14A-14B.

Figure 17A:
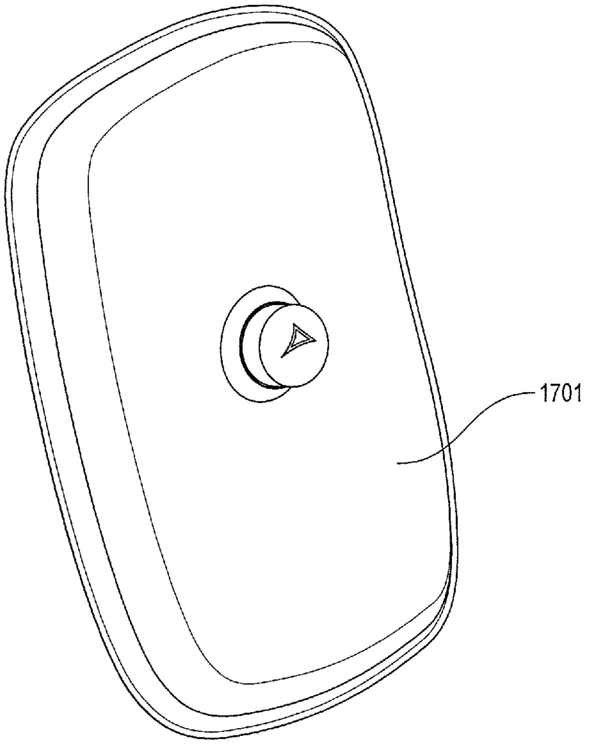
FIG. 17A is a perspective view of another variation of a dispenser.
Figure 17B:
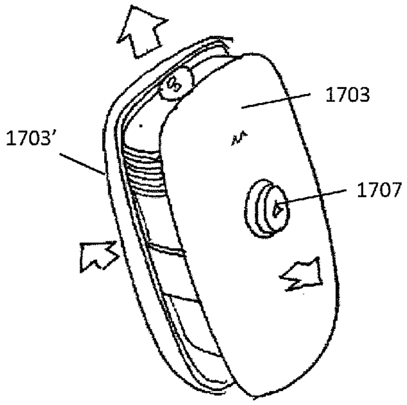
FIGS. 17B and 17C illustrate operation of the dispenser of FIG. 17A.
Figure 17C:
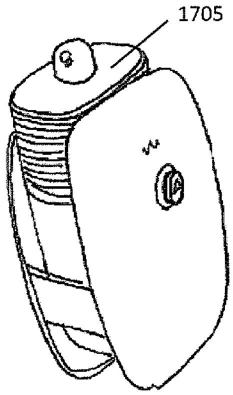

In FIGS. 17A-17C, a dispenser 1701 for a stack of nasal devices 1705 is shown in which the dispenser housing has a clam-shell design. In this variation the dispenser housing includes two halves 1703, 1703' that may be separated and opened to reveal the stack of nasal devices 1705. A button 1707 for advancing the nasal device stack (and/or for opening the dispenser) is also shown. In general, a dispenser may be opened and closed manually (e.g., by removing a cover, or pulling/pushing the dispenser housing) or automatically (but pushing a button, etc.).

Figure 18A:
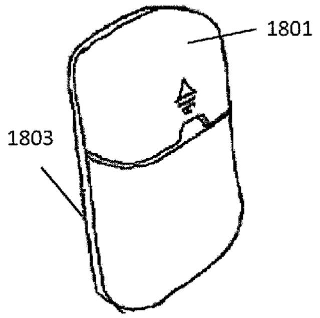
FIG. 18A is a perspective view of another variation of a dispenser.
Figure 18B:
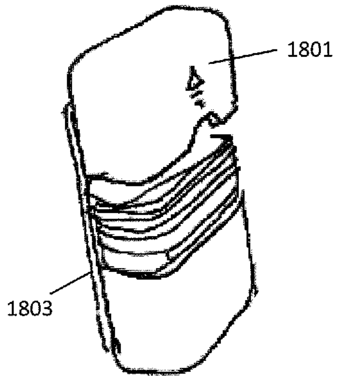
FIG. 18B illustrates operation of the dispenser of FIG. 18A.

FIGS. 18A and 18B illustrate another variation of a nasal devices dispenser. In this example the housing may be opened by sliding the cover 1801 up (as shown in FIG. 18B) to reveal the aligners. This variation also includes a mounting surface 1803. The mounting surface may be attached to a surface (e.g., a bed frame, headboard, table, wall, medicine cabinet, etc.) to affix the dispenser in place. In some variations the mounting surface mates with a mounting plate (not shown) that is affixed to another surface, to hold the dispenser against that surface. In some variations the mounting surface includes an adhesive, clamp, nail(s), screw(s), or the like, to secure the dispenser to the surface. Any of the variations of the nasal device dispensers described herein (including the hand-held variations shown in FIGS. 11A-17C) may be configured to mount to a surface.

Figure 19:
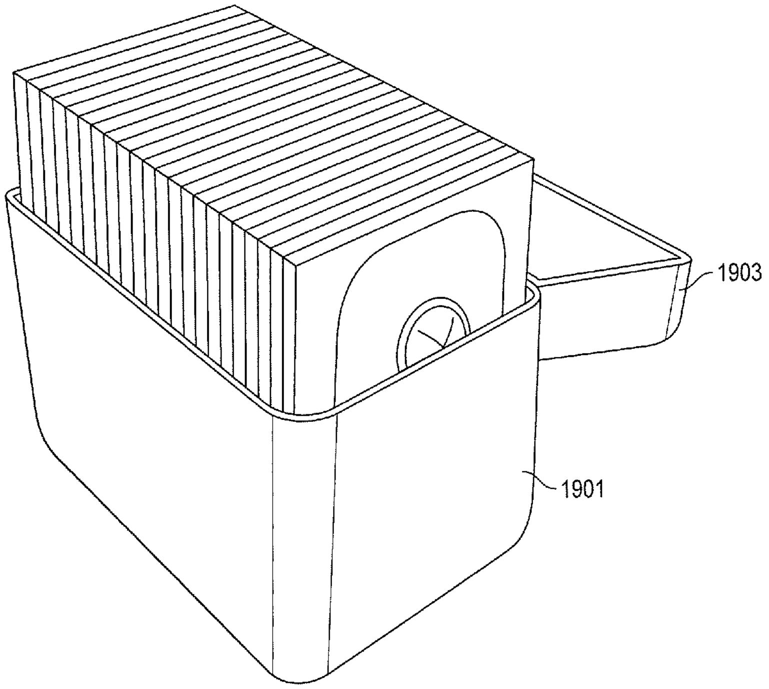
FIG. 19 illustrates a packaging system for nasal devices, as described herein.

FIG. 19 shows another variation of a dispenser having a housing 1901 that partially surrounds a plurality of nasal devices attached to a support backing. The dispenser also includes a lid 1903 that is hinged to the dispenser. In some variations the dispenser includes a plurality of support backings with releasably attached nasal devices. For example, multiple cards with pairs of nasal devices could be stored in the dispenser shown in FIG. 19.

Figure 20:
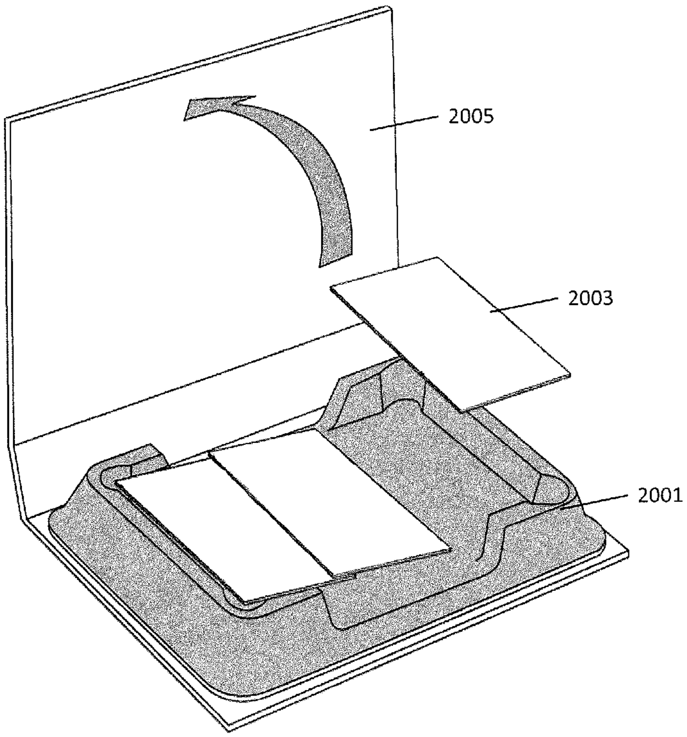
FIG. 20 is a dispenser for dispensing nasal devices.
Figure 21A:
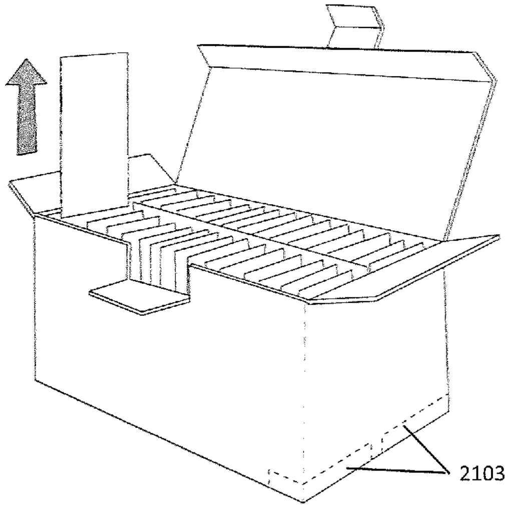
FIGS. 21A and 21B are side perspective views of a dispenser for dispensing nasal devices.
Figure 21B:
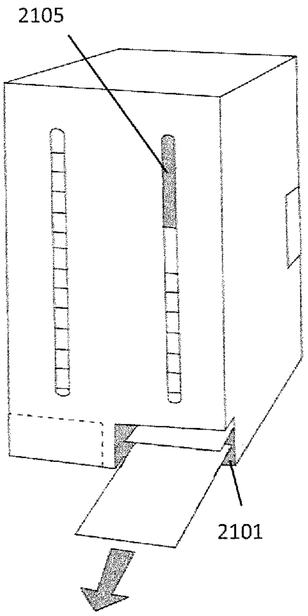

As mentioned briefly above, the dispensers, and particularly the single-use dispensers, may be used with a case configured to hold a plurality of dispensers. FIG. 20 is one variation of a case 2001 for holding multiple dispensers 2003, shown here as single-use dispensers similar to those in FIG. 10B-10C. The case may also include a housing and a lid 2005. Other examples of cases for dispensers are shown in FIGS. 21A-22A FIG. 21A shows a perspective view of a case for holding multiple single-use dispensers (although similar cases may be used to hold multi-use dispensers, or refills for multi-use dispensers). The case may include an opening 2101 (or a region that can be opened 2103) through which the single use dispensers can be withdrawn, as shown in FIG. 21B. This case also includes an indicator (shown here as a window 2105) that indicates how many single-use dispensers are left in the case.

Figure 21C:
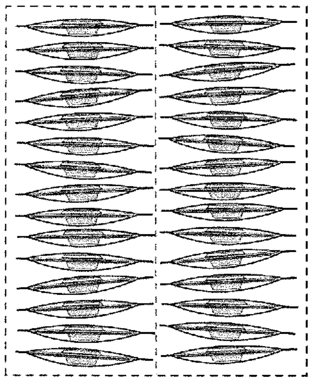
FIG. 21C is a top view of the dispenser shown in FIGS. 21A and 21B.
Figure 22A:
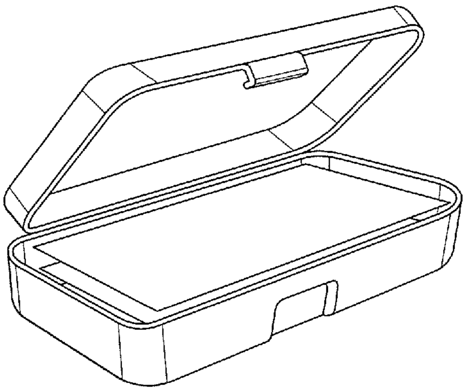
FIGS. 22A and 22B are cases for nasal device dispensers and nasal devices.
Figure 22B:
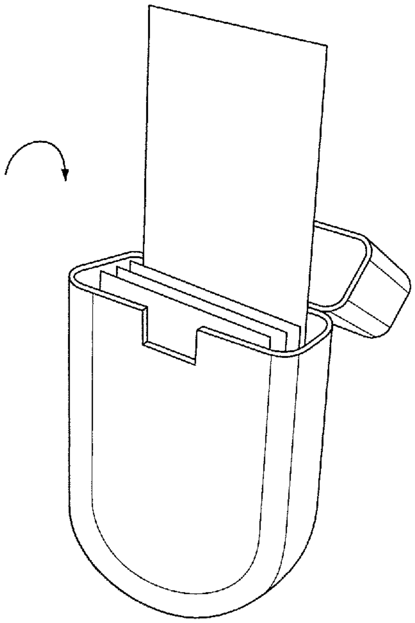

FIG. 21C is a top view of the case in which the case has been made transparent (indicated by the dashed lines), showing the plurality of single-use dispensers held within the case. FIGS. 22A and 22B illustrate smaller cases for holding single-use dispensers.

Figure 23A:
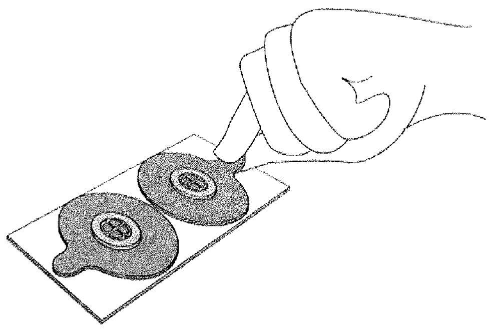
FIGS. 23A-23B illustrate one method of dispensing a nasal device.
Figure 23B:
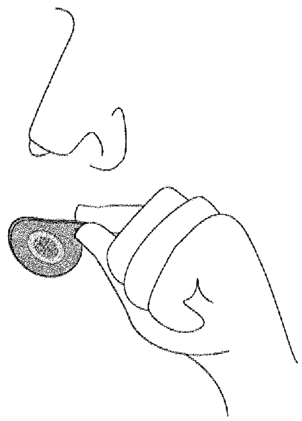
Figure 24A:
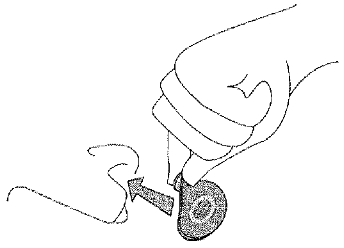
FIGS. 24A-24D illustrate one method of applying a nasal device dispensed from a dispenser.
Figure 24B:
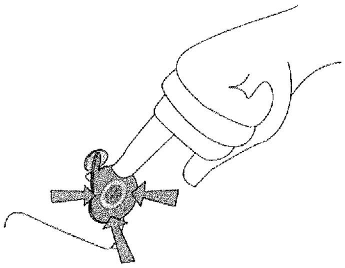
Figure 24C:
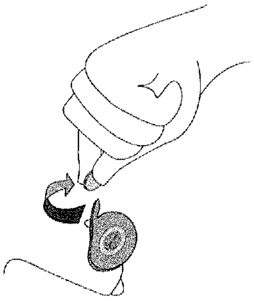
Figure 24D:
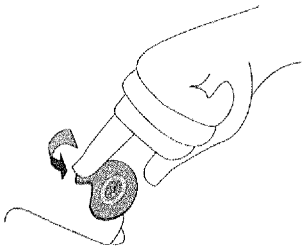

In operation, an adhesive nasal device may be dispensed by removing the nasal device from the support backing and applying the device to the subject's nose. This is illustrated for one variation of a system for dispensing nasal devices in FIGS. 23A and 23B. In FIG. 23A the system for dispensing nasal devices includes a pair of nasal devices that are removably attached to a card (a support backing) as described for FIGS. 4A and 4B. Once the device has been dispensed from a dispenser, it may be secured in communication with a subject's nostril, as illustrated in FIGS. 24A-24D.

Figure 25:
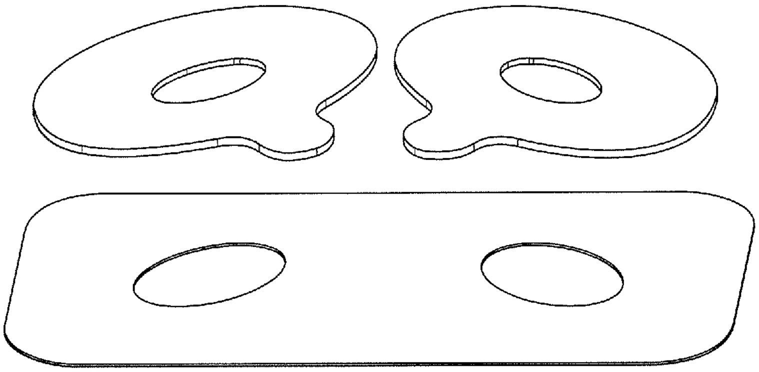
FIG. 25 illustrates one variation of a plurality of nasal devices aligned for attachment to a support backing.

As described above, a packaging system for a nasal device may include a support backing having an opening through which the airflow resistor of a nasal device may be aligned, as illustrated in FIG. 25. In FIG. 25, the support backing ("liner card") includes two openings ("thru hole") that may be aligned with the airflow resistor regions of adhesive nasal devices. In FIG. 25, the nasal device includes an adhesive holdfast ("adhesive) that is removably secured to the support backing. An airflow resistor may be positioned in the opening through the adhesive holdfast. The nasal device(s) may be assembled on the support backing. For example, as illustrated in FIG. 25, the adhesive holdfast portion of the nasal device may be applied to a support backing with the openings through the support backing and the holdfast aligned. The airflow resistor (including those described above in FIGS. 1A-2B) may then be secured across the opening through the holdfast, thereby aligning them with the opening through the support backing.

In any of these variations, the nasal device, and particularly the airflow resistor of the nasal device, may be tested because the opening through the support backing allows air to pass through the nasal device when the nasal device is secured to the support backing. For example, the resistance through the nasal device may be tested by measuring the resistance to airflow applied in the direction of exhalation when the device is worn, and/or the direction of inhalation when the device is worn.

Figure 26:
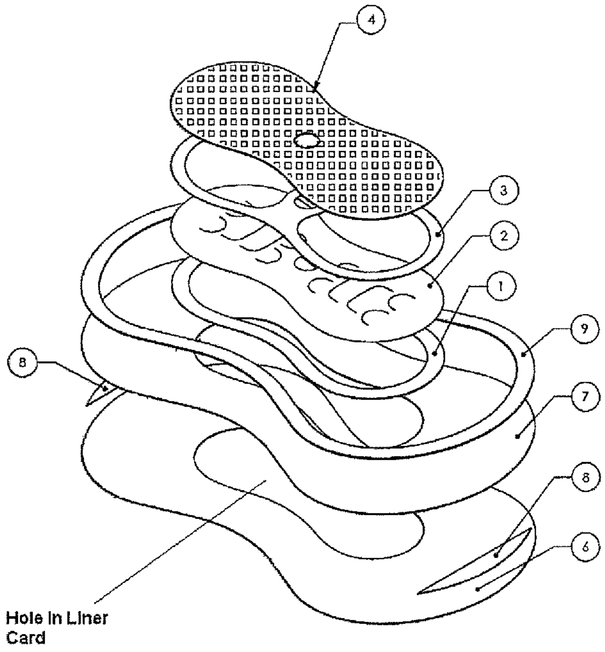
FIG. 26 illustrates another variation of a nasal device that may be used with any of the packaging systems described herein.

FIG. 26 is an exploded view of another variation of a nasal device that may be used with any of the packaging systems and methods described herein. In FIG. 26, each layer forming the whole-nose nasal device illustrated is labeled. The airflow resistor portion of the device is formed by a mesh layer 1 and a flap valve layer 2 that are secured together by an adhesive 3 (double sided adhesive layer) 3. This airflow resistor is adhesively secured to a holdfast layer 7 that includes a biocompatible adhesive for securing the device to a subject. A double-sided adhesive 1 is used to secure the airflow resistor to the holdfast. The holdfast 7 also includes a rim 9 that may provide stiffness to the edge of the device, since the holdfast layer 7 may be made of a thin and flexible material that can conform to the subjects nose and seal against it.

In FIG. 26, the nasal device is affixed to a support backing layer 6. Although many of the support backing layers illustrated above are cards that are larger or extend beyond the perimeter of the nasal devices that are attached to them, the support backing may also be smaller, or the same general size as the nasal device, as illustrated in FIG. 26. This variation also includes a removal tab 2 that may provide a non-adhesive region for removal of the device. The support backing (layer 6) also includes an opening that is aligned with the airflow resistor, as described above.

Figure 27A:
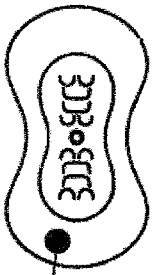
FIGS. 27A and 27B illustrate a nasal device such as the one shown in FIG. 26 packaged on a support backing within a dispenser housing shown as pouch.
Figure 27B:
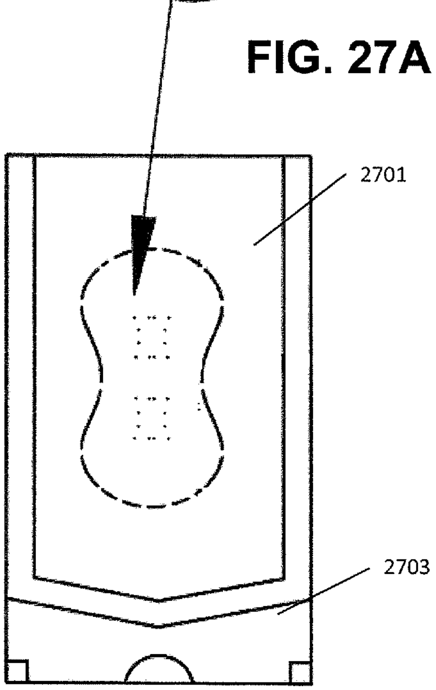

FIG. 27A illustrates a nasal device such as the one shown in FIG. 26 that can be applied to a card-like support backing 2701 as illustrated in FIG. 27B. In this example, the nasal device shown in FIG. 27A is removably secure to the card (support backing), and they are both placed in a dispenser housing (pouch 2703). This pouch may be made of plastic, foil, paper, etc. as described above. The pouch may be sealed, and (in some variations) may be treated to sterilize the nasal device within.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A method of packaging nasal devices having an airflow resistor that is configured to inhibit nasal exhalation more than inhalation, the method comprising:
   aligning the airflow resistor with an opening through a support backing;
   removably securing the nasal device to the support backing; and
   sealing the support backing and removably secured nasal device within a dispenser housing.

2. The method of claim 1, wherein sealing the support backing within the dispenser housing comprises sealing the support backing and removably secured nasal device within a pouch.

3. The method of claim 1, wherein sealing the support backing within the dispenser housing comprises placing the support backing and removably secured nasal device within a tray.

4. The method of claim 1, further comprising testing the resistance of the airflow resistor of the nasal device after it has been removably secured to the support backing.

5. The method of claim 1, further comprising sterilizing the dispenser housing.

6. The method of claim 1, further comprising forming the opening in the support backing.

7. The method of claim 1, wherein removably securing the nasal device to the support backing comprises adhesively securing the nasal device to the support backing.

8. The method of claim 1, further comprising applying an adhesive layer to the support backing.

9. The method of claim 1, further comprising testing the resistance through the airflow resistor with the nasal device secured to the support backing by measuring the resistance to airflow applied in the direction of exhalation when the device is worn.

10. The method of claim 1, further comprising testing the resistance through the airflow resistor with the nasal device secured to the support backing by measuring the resistance to airflow applied in the direction of inhalation when the device is worn.

11. A method of packaging nasal devices having an airflow resistor that is configured to inhibit nasal exhalation more than inhalation, the method comprising:
   aligning the airflow resistor with an opening through a support backing;
   removably securing the nasal device to the support backing; and
   testing the resistance through the airflow resistor when the nasal device is secured to the support backing by measuring the resistance to airflow applied through the airflow resistor.

12. The method of claim 11, further comprising sealing the support backing and removably secured nasal device within a dispenser housing.

13. The method of claim 12, further comprising sterilizing the dispenser housing.

14. The method of claim 11, wherein testing the resistance comprises measuring the resistance to airflow applied in the direction of inhalation when the device is worn.

15. The method of claim 11, wherein testing the resistance comprises measuring the resistance to airflow applied in the direction of exhalation when the device is worn.

16. The method of claim 11, further comprising forming the opening in the support backing.

17. The method of claim 11, wherein the step of removably securing the nasal device to the support backing comprises adhesively securing the nasal device to the support backing.

18. The method of claim 11, further comprising applying an adhesive layer to the support backing.

19. A method of packaging nasal devices having an airflow resistor that is configured to inhibit nasal exhalation more than inhalation, the method comprising:

forming an opening through a support backing, wherein the support backing comprises a sheet of material;

assembling the airflow resistor in the opening through the support backing; and testing the resistance through the assembled airflow resistor in the opening of the support backing by measuring the resistance to airflow applied through the airflow resistor.

* * * * *